US011844627B2

United States Patent
Gelman et al.

(10) Patent No.: US 11,844,627 B2
(45) Date of Patent: *Dec. 19, 2023

(54) CATHETER FORCE CONTROL DEVICE

(71) Applicant: THE UNIVERSITY OF WESTERN ONTARIO, London (CA)

(72) Inventors: Daniel Gelman, London (CA); Allan Skanes, London (CA); Maria Drangova, London (CA)

(73) Assignee: The University of Western Ontario, London (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/932,989

(22) Filed: Sep. 16, 2022

(65) Prior Publication Data
US 2023/0017179 A1 Jan. 19, 2023

Related U.S. Application Data

(63) Continuation of application No. 16/875,630, filed on May 15, 2020, now Pat. No. 11,445,977, which is a
(Continued)

(51) Int. Cl.
*A61B 5/00* (2006.01)
*A61B 34/20* (2016.01)
(Continued)

(52) U.S. Cl.
CPC ........ *A61B 5/6852* (2013.01); *A61B 18/1492* (2013.01); *A61B 34/20* (2016.02);
(Continued)

(58) Field of Classification Search
CPC ..... A61B 5/6852; A61B 5/1107; A61B 5/113; A61B 5/7207; A61B 90/06;
(Continued)

(56) References Cited

U.S. PATENT DOCUMENTS

| 5,159,861 A | 11/1992 | Anderson |
| 6,004,271 A | 12/1999 | Moore |

(Continued)

FOREIGN PATENT DOCUMENTS

| CN | 101947130 A | 1/2011 |
| WO | WO 2011/137336 A1 | 11/2011 |

OTHER PUBLICATIONS

International Search Report in PCT/CA2017/050119 dated May 15, 2017.
(Continued)

*Primary Examiner* — Eun Hwa Kim
*Assistant Examiner* — Catherine Premraj
(74) *Attorney, Agent, or Firm* — Knobbe Martens Olson & Bear LLP

(57) ABSTRACT

A device including a base sized to be hand-held, the base defining a longitudinal axis between first and second opposing longitudinal ends, a cover reversibly fastened to the base in a closed position; a sheath clamp coupled to the base, the sheath clamp capturing a sheath handle of a sheath to immobilize the sheath handle relative to the base, wherein the sheath clamp is an aperture formed in corresponding abutting edges of the cover and the base, the aperture being formed when the cover and the base are in the closed position; a catheter clamp capturing a catheter, a remote end of the catheter configured to deliver a catheterized medical procedure; the catheter clamp aligned to be substantially co-axial with the sheath clamp; and a linear actuator effecting back-and-forth linear motion of the catheter clamp relative to the sheath clamp.

20 Claims, 22 Drawing Sheets

Related U.S. Application Data continuation of application No. 16/074,753, filed as application No. PCT/CA2017/050119 on Feb. 2, 2017, now Pat. No. 10,667,752.

(60) Provisional application No. 62/290,243, filed on Feb. 2, 2016.

(51) Int. Cl.

| | | |
|---|---|---|
| *A61B 18/14* | (2006.01) | |
| *A61B 90/00* | (2016.01) | |
| *A61M 25/01* | (2006.01) | |
| *A61B 18/00* | (2006.01) | |
| *A61B 18/02* | (2006.01) | |
| *A61B 5/113* | (2006.01) | |
| *A61B 5/11* | (2006.01) | |

(52) U.S. Cl.
CPC ............. *A61B 90/06* (2016.02); *A61M 25/01* (2013.01); *A61B 5/113* (2013.01); *A61B 5/1107* (2013.01); *A61B 5/7207* (2013.01); *A61B 2018/00351* (2013.01); *A61B 2018/00529* (2013.01); *A61B 2018/0212* (2013.01); *A61B 2090/065* (2016.02); *A61B 2505/05* (2013.01); *A61B 2562/0261* (2013.01); *A61M 2025/0166* (2013.01)

(58) Field of Classification Search
CPC .......... A61B 18/1492; A61B 2090/065; A61B 2018/00351; A61B 2018/00529; A61B 2018/0212; A61B 2505/05; A61B 2562/0261; A51B 34/20; A61M 25/01; A61M 2025/0166

See application file for complete search history.

(56) References Cited

U.S. PATENT DOCUMENTS

| | | |
|---|---|---|
| 8,528,565 B2 | 9/2013 | Hauck et al. |
| 8,900,225 B2 | 12/2014 | Bar-Tal et al. |
| 2006/0084964 A1 | 4/2006 | Knudson et al. |
| 2006/0241421 A1 | 10/2006 | Rahn et al. |
| 2009/0076445 A1* | 3/2009 | Furnish .................. A61M 25/01 604/95.01 |
| 2010/0298826 A1 | 11/2010 | Leo et al. |
| 2011/0015648 A1 | 1/2011 | Alvarez et al. |
| 2012/0184955 A1* | 7/2012 | Pivotto .................. A61B 34/30 606/41 |
| 2013/0137963 A1 | 5/2013 | Olson |
| 2013/0190726 A1 | 7/2013 | Kesner et al. |
| 2013/0325035 A1 | 12/2013 | Hauck et al. |
| 2014/0249653 A1 | 9/2014 | Blevins et al. |
| 2015/0073339 A1 | 3/2015 | Pacheco et al. |
| 2015/0141914 A1* | 5/2015 | Fasano ............... A61M 25/0113 604/95.01 |

OTHER PUBLICATIONS

Partial Supplemental European Search Report in European Application No. 17746678.6, dated Aug. 20, 2019.

Dominici et al. (2015). Cascade force control for autonomous beating heart motion compensation: Control Engineering Practice, vol. 37: pp. 80-88.

Kesner et al. (2011) Position Control of Motion Compensation Cardiac Catheters: IEEE Trans Robot., Jul. 21, 2011; PP(99): pp. 1-11.

Kesner et al. (2011) Force Control of Flexible Catheter Robots for Beating Heart Surgery: IEEE Int Conf Robot Autom. 2011 : pp. 1589-1594.

Kesner et al. (2014) Robotic catheter cardiac ablation combining ultrasound guidance and force control: The International Journal of Robotics Research, vol. 33(4): pp. 631-644.

Yuen et al. (2008) 3D Ultrasound-Guided Motion Compensation System for Beating Heart Mitral Valve Repair: Med Image Comput Comput Assist Interv., vol. 11 (Pt 1): pp. 711-719.

Zarrouk et al. (2013) Force feedback control for compensation of physiological motions in beating heart surgery with real-time experiments. Proceedings of the 3rd International Conference on Systems and Control, Algiers, Algeria, Oct. 29-31, 2013.

* cited by examiner

FIG. 1
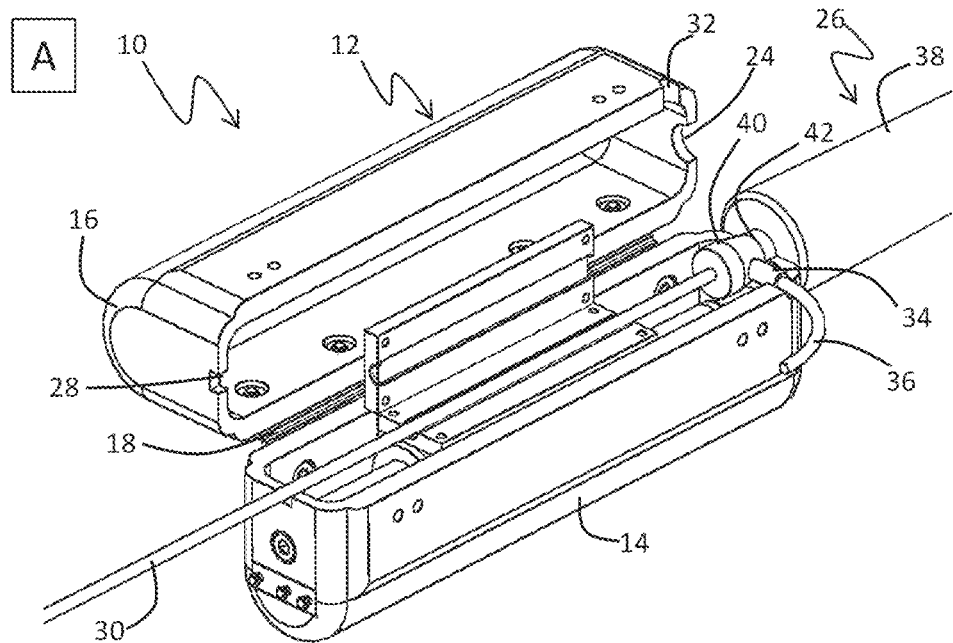
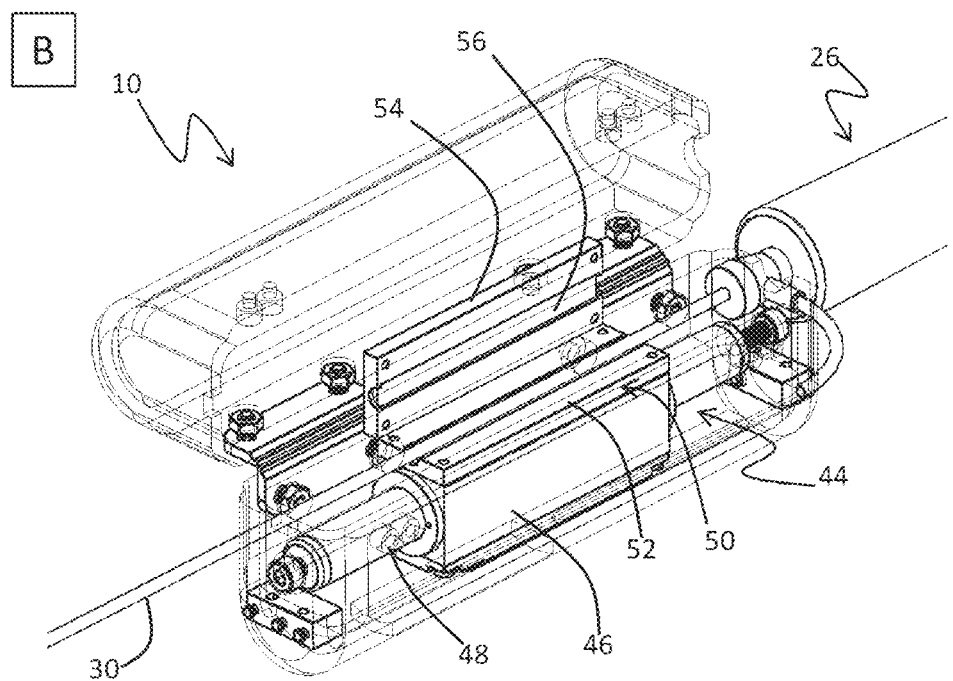

FIG. 2
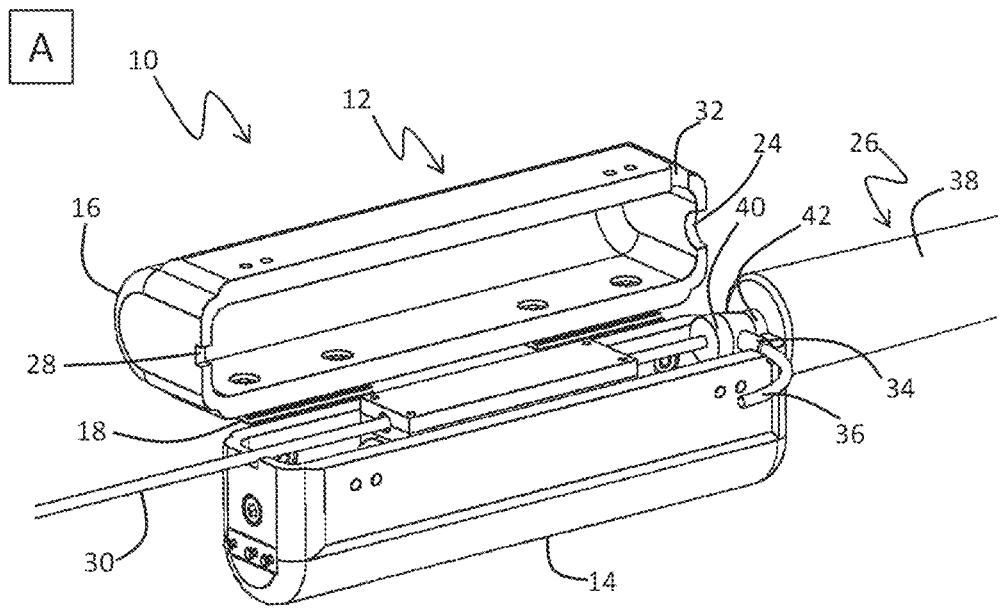
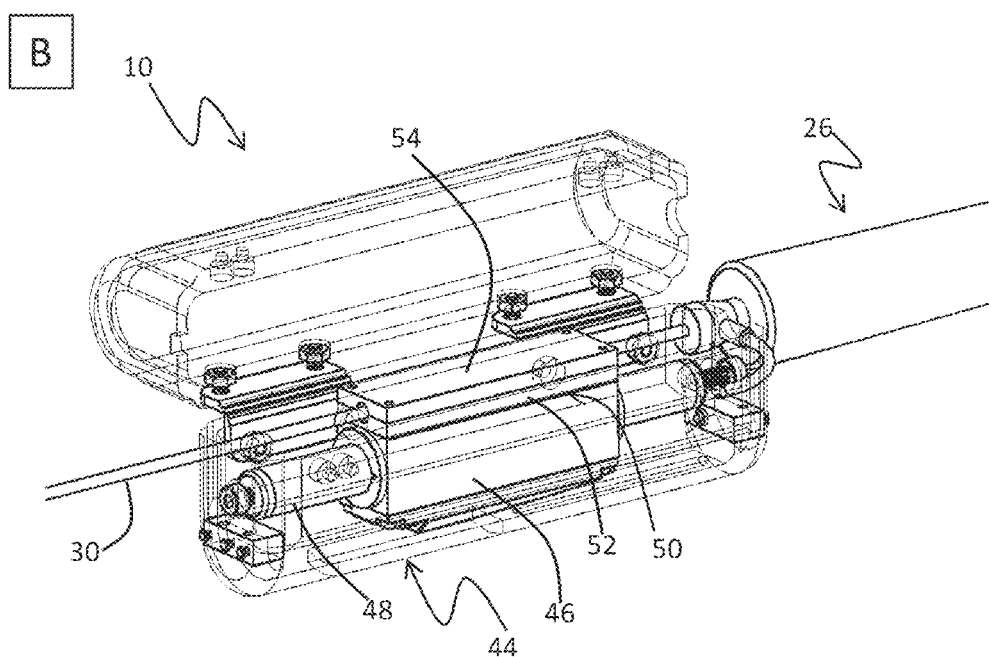

FIG. 15
A
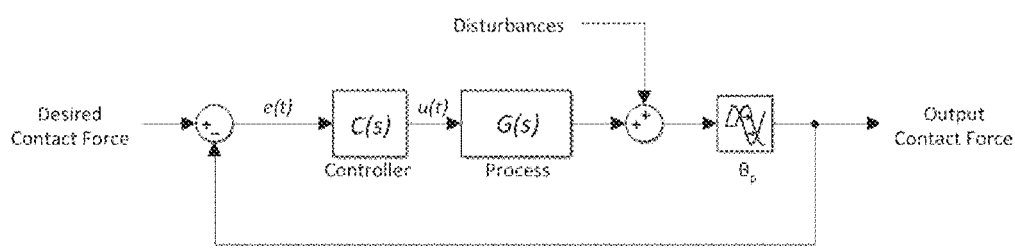
B
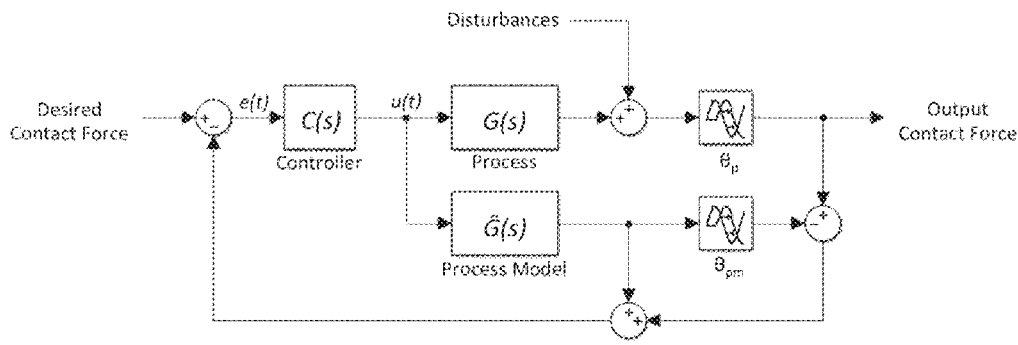
C
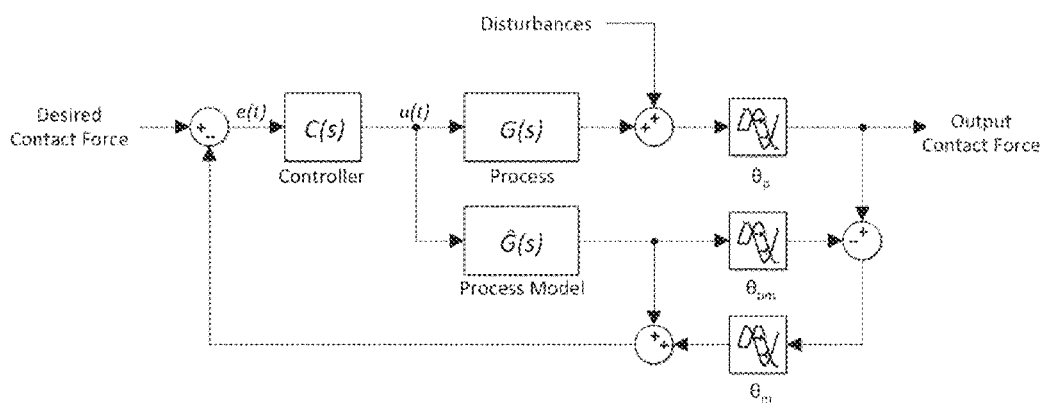

FIG. 15 (cont'd)
D
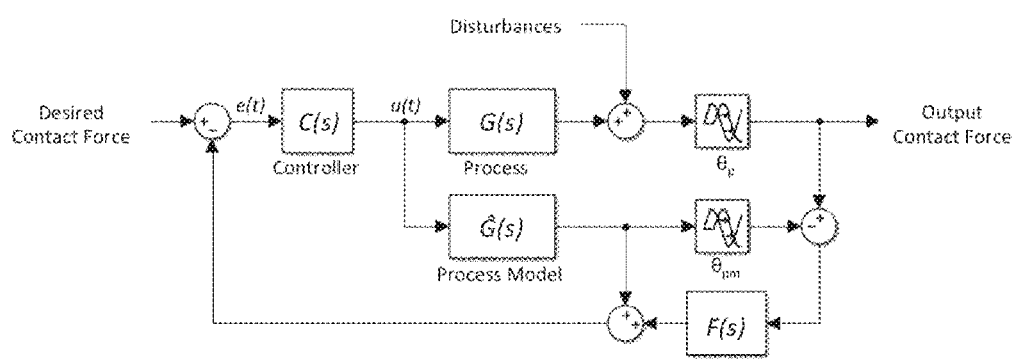
E
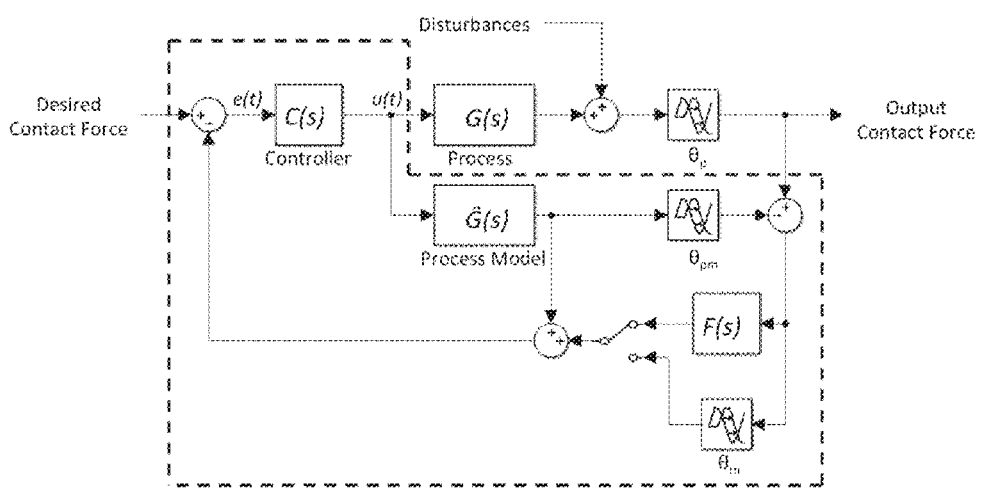

FIG. 17
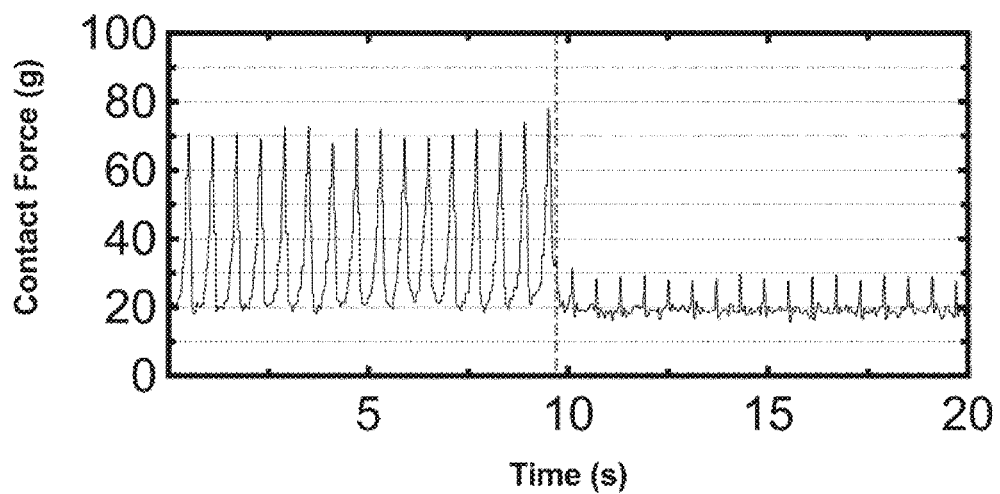
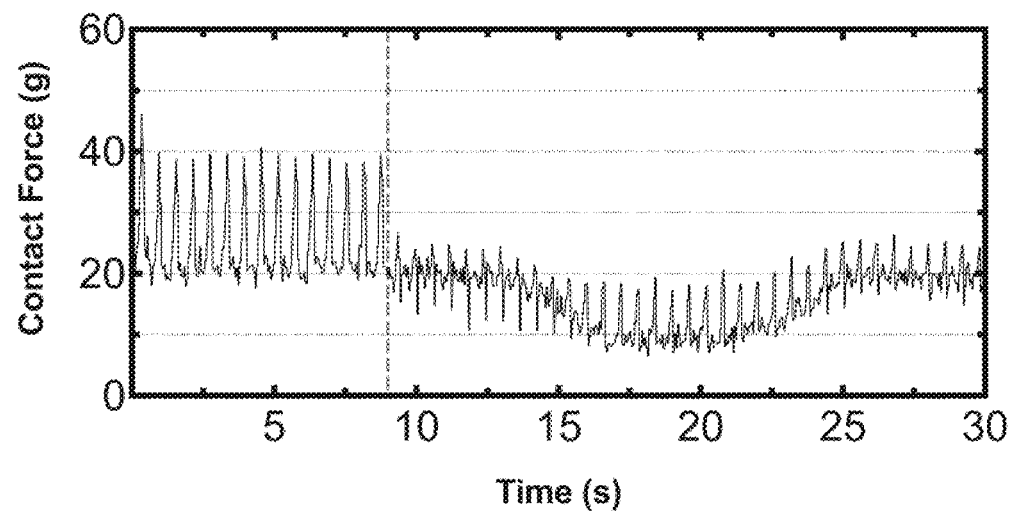

FIG. 17 (cont'd)
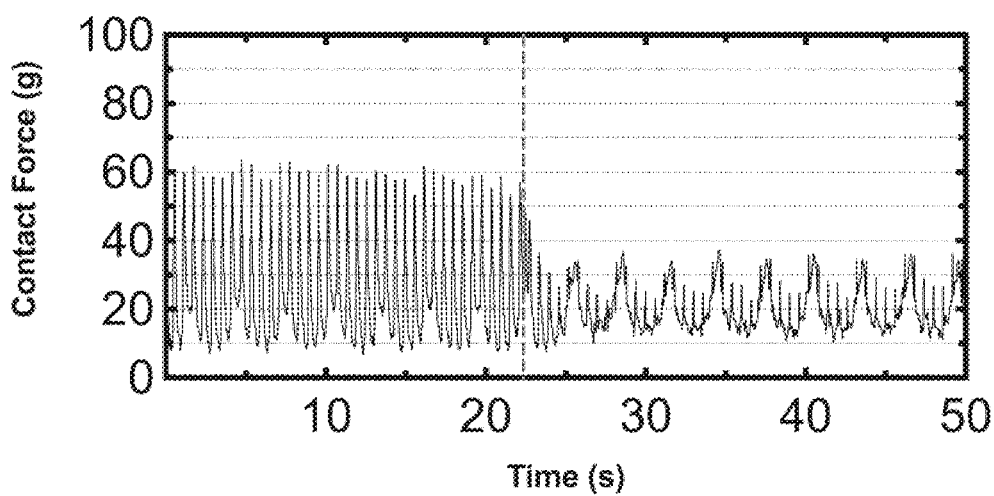
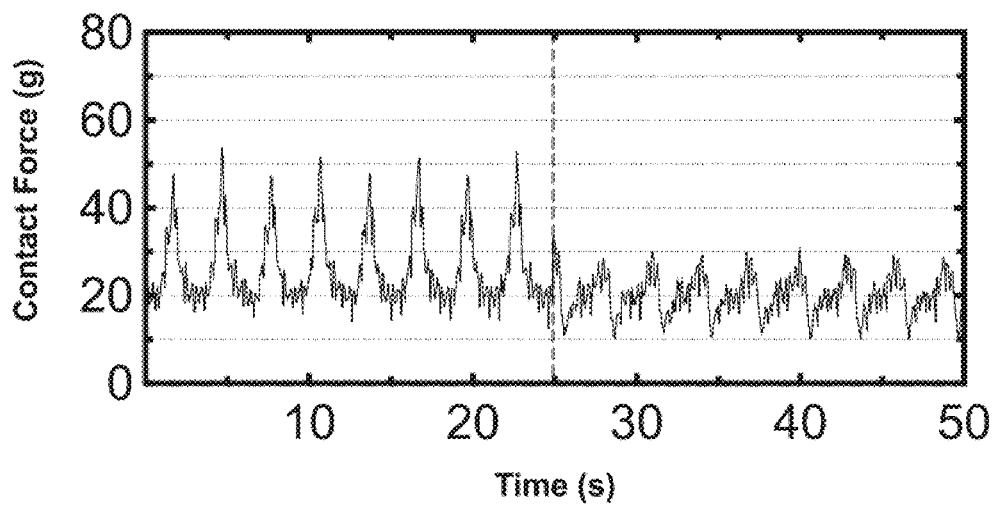

FIG. 18
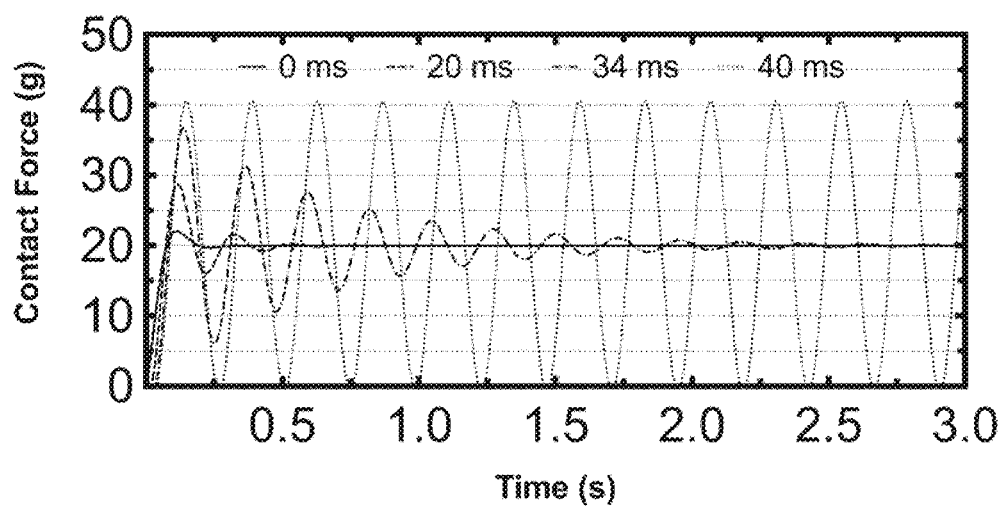
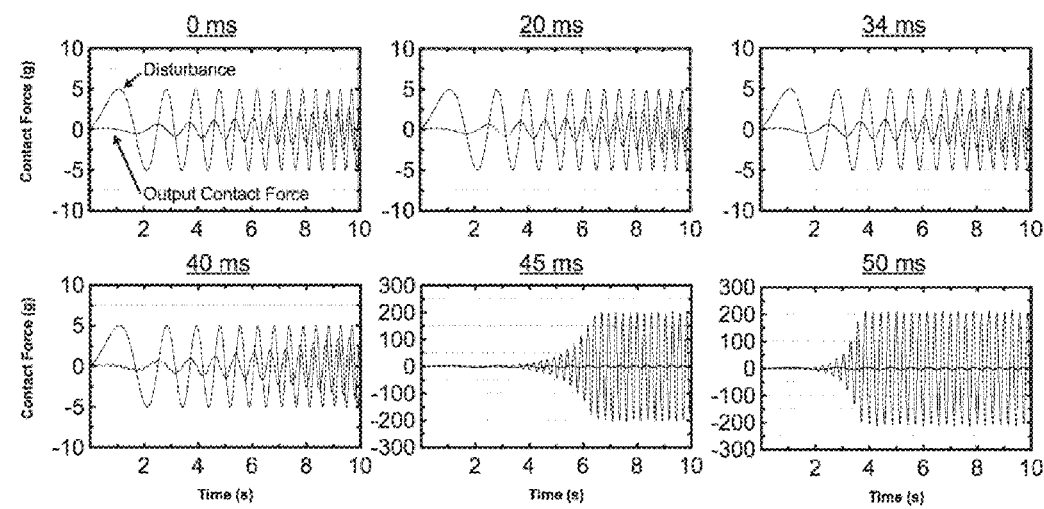

CATHETER FORCE CONTROL DEVICE

CROSS REFERENCE TO RELATED APPLICATIONS

This application is a continuation of U.S. application Ser. No. 16/875,630, filed May 15, 2020, which is a continuation of U.S. application Ser. No. 16/074,753, filed Aug. 1, 2018, which is the U.S. National Phase of International Application No. PCT/CA2017/050119, filed Feb. 2, 2017, designating the U.S. and published in English as WO 2017/132768 A1 on Aug. 10, 2017, which claims the benefit of U.S. Provisional Patent Application No. 62/290,243 filed Feb. 2, 2016. Any and all applications for which a foreign or domestic priority claim is identified here or in the Application Data Sheet as filed with the present application are hereby incorporated by reference under 37 CFR 1.57.

BACKGROUND OF THE INVENTION

Field of the Invention

The present invention relates to catheterized medical procedures, and more particularly to automated control of catheter contact-force with a target tissue.

Description of the Related Art

The use of catheters as a medical intervention tool continues to grow in popularity. For example, many cardiac and vascular surgical procedures benefit from catheterization, as surgical procedures can involve large incisions including cutting of bone and surrounding soft tissue. Recovery time for patients can often be reduced by replacing an invasive surgical procedure with a catheter procedure.

Percutaneous radiofrequency (RF) catheter ablation is an example of a catheter based procedure that is becoming the standard of care for a variety of cardiac arrhythmias. Cardiac interventionalists introduce ablation catheters into the heart and manipulate them until the distal tip contacts the targeted myocardium. Once reached, RF power is delivered to form ablation lesions that interrupt the electrical pathways responsible for the arrhythmia. For successful treatment it is important that these lesions are transmural, as superficial lesions leave areas of healthy myocardium that may result in conduction recurrence and ablation failure. For successful treatment the contact force of the catheter tip onto the tissue needs to be held within a desired range of contact force. Due to motion of the target tissue, the myocardial wall, interventionalists that manually control the catheter—typically, by observing real time contact force data provided by a catheter type sensor—are incapable of maintaining the desired contact force range for a necessary time period.

Manual operation of a catheter presents risk associated with insufficient contact force or excessive contact force compared to the desired range. Insufficient contact force presents a risk of an ineffective ablation lesion with patients requiring repeat treatments. A procedure delivered with excessive contact force presents a risk of deep tissue overheating, which may result in "steam pop", perforation and injury outside the heart, including esophageal, pulmonary and phrenic nerve damage.

These potential risks of injury associated with excessive contact force often inhibit interventionalists and cause them to deliver the ablation lesion tentatively, erring towards a lower level contact force.

Accordingly, there is a continuing need for automated control of catheter contact-force with a target tissue.

SUMMARY OF THE INVENTION

In an aspect there is provided a hand-held catheter force control device comprising:
  a linear actuator;
  a clamp for connecting a catheter to the linear actuator;
  the linear actuator controlling contact-force between the catheter and a target tissue.

In another aspect there is provided a hand-held catheter force control device comprising:
  an elongate base sized to be hand-held, the base defining a longitudinal axis between first and second opposing longitudinal ends;
  a linear actuator mounted to the base to provide linear motion substantially parallel to the longitudinal axis of the base;
  a sheath clamp coupled to the base, the sheath clamp sized to fixedly capture a sheath handle;
  a catheter clamp coupled to the linear actuator, the catheter clamp sized to fixedly capture a catheter; and
  the catheter clamp aligned to be substantially co-axial with the sheath clamp.

In further aspects, systems and methods incorporating the catheter contact-force control device are provided.

BRIEF DESCRIPTION OF THE DRAWINGS

FIG. 1 shows a CFC device 10 having a catheter clamp in an open position in (A) an isometric view and (B) an isometric wireframe view;

FIG. 2 shows the CFC device 10 having a catheter clamp in a closed position in (A) an isometric view and (B) an isometric wireframe view;

FIG. 15 (A) shows a first schematic representation of a control algorithm for controlling the CFC device. (B) shows a second schematic representation of a control algorithm for controlling the CFC device. (C) shows a third schematic representation of a control algorithm for controlling the CFC device. (D) shows a fourth schematic representation of a control algorithm for controlling the CFC device; (E). shows a fifth schematic representation of a control algorithm for controlling the CFC device.

as shown in FIG. 15C). (C) shows a third CF profile in a simulation using a control algorithm shown in FIG. 15, i.e., a simulation that shows a comparison between SP (as shown in FIG. 15B) and SP with a respiratory disturbance modifier (SP with F(s); as shown in FIG. 15D).

FIG. 17 (A) shows a CF profile recorded during pig experiments using the CFC device to control catheter contact force at a target location in a pig heart, i.e., results from an experiment performed in the left atrium of a pig. (B) a recorded CF profile from another experiment in the right atrium of the pig heart. (C) A reduction of cardiac disturbances, but little to no reduction in respiratory motion disturbances (experiment performed in the left atrium of the pig). (D) Results from another experiment in a pig—the right atrial septum is dominated by respiratory motion while cardiac motion is minimal.

FIG. 18 Simulation CF profiles demonstrating effect of deadtime on a PID control algorithm. (A) shows several plots that may be compared for a stability analysis (B) shows several plots that may be compared to analyze disturbance rejection.

DETAILED DESCRIPTION OF PREFERRED EMBODIMENTS

Figure 3:
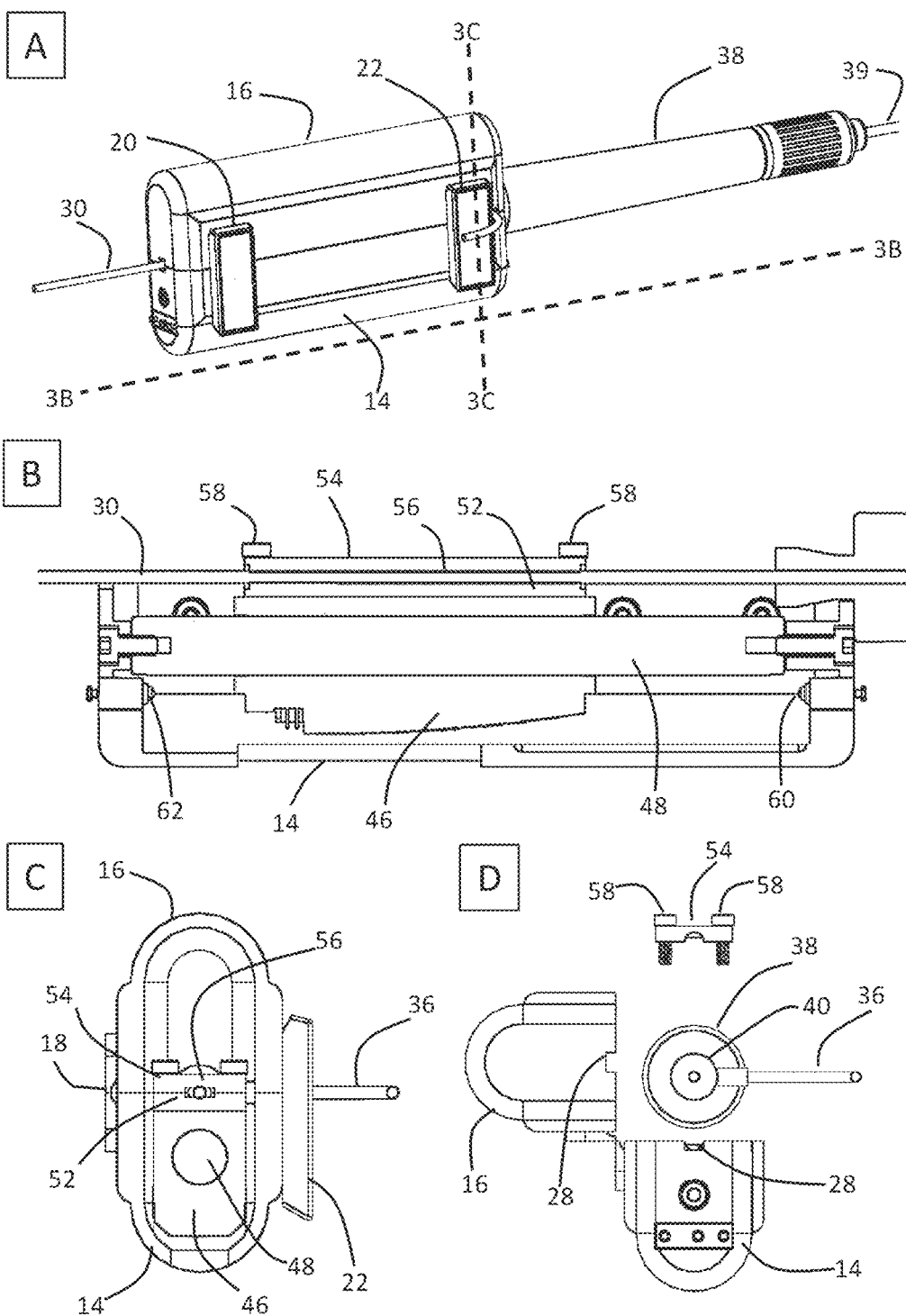
FIG. 3 shows (A) an isometric view of the CFC device 10 with the housing in a closed position, (B) an axial cross-section view, (C) a lateral cross-section view, and (D) an exploded back-end elevational view.

Referring to the drawings, various views of a catheter force controller (CFC) device 10 are shown in FIGS. 1 to 3.

FIGS. 1 and 2 both show isometric views with (A) a housing 12 illustrated as a solid object hiding a view of interior components and (B) the housing 12 illustrated in wireframe to visualize interior components. FIG. 1 shows the CFC device 10 disengaged from a catheter 30 while FIG. 2 shows the CFC device 10 engaged to the catheter 30. FIG. 3A is also an isometric view of the CFC device 10, but differs from FIGS. 1 and 2 in that a cover 16 of the housing 12 is in a closed position. FIG. 3B shows an axial cross-section view taken along line 3B-3B. FIG. 3C shows a lateral cross-section view taken along line 3C-3C. FIG. 3D shows an exploded back-end elevational view.

The housing 12 of the CFC device 10 comprises a base 14 and a cover 16. The base 14 and cover 16 are substantially symmetrical. Both are elongate, rigid, trough-shaped boxes defining an interior chamber having substantially equal longitudinal and lateral dimensions sized to be conveniently held by one hand. The base 14 defines an open top and the cover 16 defines a corresponding open bottom that are aligned to each other for open communication between their respective interior chambers when the base 14 and cover 16 are placed in a closed position. The base 14 is pivotably coupled to cover 16 by hinge 18 with each arm of the hinge 18 joining a corresponding edge contouring the open top of the base 14 and the open bottom of the cover 16, so that the open top and bottom are aligned when the base 14 and the cover 16 are in the closed position. First latch 20 and second latch 22 (shown in FIG. 3A) are placed on an opposing edge to hinge 18 to reversibly fasten the base 14 and cover 16 in a closed position.

The housing 12 defines several apertures for receiving structural components of a catheter-sheath combination. Each of the apertures is communicative with the interior chambers of the base 14 and cover 16. Each of the apertures is formed when the base 14 and cover 16 are in a closed position with a part of the aperture defined in the perimeter contouring the open top of base 14 and the remainder of each aperture defined in a corresponding location in the perimeter contouring the open bottom of the cover 16. A first aperture 24, formed by alignment of mated semi-circular cutouts defined at corresponding first ends of the base 14 and cover 16, is sized to clamp sheath handle 26 so that sheath handle is fixed to housing 12 and remains stationary relative to the housing 12 when the base 14 and cover 16 are in a closed position. A second aperture 28, formed by alignment of mated rectangular cutouts defined at corresponding second ends of the base 14 and cover 16, is sized to allow free sliding passage of catheter 30 so that catheter 30 can move relative to housing 12 and sheath handle 26 when the base 14 and cover 16 are in a closed position. The first and second apertures are defined at first and second ends of the housing 12 to be in opposition across the longitudinal dimension of the housing 12 and to be substantially co-axial so that the catheter 30 can be supported linearly as it spans the longitudinal dimension of base 14 from the first aperture 24 to the second aperture 28. A third aperture 32, formed by alignment of mated semi-circular cutouts defined at a corresponding side location proximal to the first ends of the base 14 and cover 16, is sized to receive side port 34, which extends radially outward from sheath handle 26, so that side port 34 can maintain a connection with water line 36 when the base 14 and cover 16 are in a closed position. Water line 36 supplies a suitable liquid, such as an isotonic saline solution, to reduce friction between the sheath and catheter and provide irrigation during RF application, for example to provide cooling and/or drug delivery. The axis of third aperture 32 is aligned substantially perpendicular to the axis of first aperture 24 to accommodate the radial orientation of side port 34. The second aperture may be interchangeably referred to as a guide aperture. The third aperture may be interchangeably referred to as a side port aperture.

The sheath handle 26 comprises a tubular body 38 with an entry valve for insertion of a catheter 30. A first end of the entry valve supports a hemostatic seal 40 defining an insertion point sized to receive catheter 30 while a second end of the entry valve forms a neck 42 integrally connected with a terminal shoulder of the tubular body 38. Neck 42 is located in between hemostatic seal 40 and tubular body 38 and neck 42 has a smaller diameter than both hemostatic seal 40 and tubular body 38. Therefore, sizing the first aperture 24 to capture or clamp neck 42 and buttressing the first end of the housing 12 against the terminal shoulder of the tubular body 38 that joins neck 42 effectively prevents motion of the sheath handle when base 14 and cover 16 are in a closed position.

A linear actuator 44 is mounted within the interior chamber of base 14. The linear actuator 44 is a sled and slide track mechanism having a single Degree of Freedom providing back-and-forth linear motion. The sled is a coil assembly 46 and the slide track is a magnetic rod 48. The coil assembly 46 contained within a suitable housing with bushings is mounted on the magnetic rod 48 which in turn is mounted to base 14. A first limit switch 60 is mounted to the first end of base 14 and a second limit switch 62 is mounted to the second end of base 14. First and second limit switches are used for a homing protocol and may also be used as over-travel or end-of-range kill switches during operation of the CFC device 10.

During operation, the linear actuator 44 is communicative with a controller. A connector port (not shown), for receiving control signals from a controller/driver circuit with communication to the linear actuator, is mounted within base 14 with the connector port (not shown) accessible from an exterior surface of the base 14 to connect a corresponding connector cable (not shown) from the controller/driver circuit.

A catheter clamp 50 is mounted to the housing of the coil assembly 46. The catheter clamp 50 comprises an elongate bottom plate 52 and a matching equally dimensioned top plate 54. Bottom plate 52 is mounted to the housing of coil assembly 46 and top plate 54 is reversibly fastened to bottom plate 52 with bolts 58. Bolts 58 extend through bores formed in top plate 54 and are rotated to threadingly engage blind threaded bores formed in bottom plate 52. Top plate 54 and bottom plate 52 may be pivotably coupled along a common edge to reduce the number of bolts needed to reversibly fasten the catheter clamp 50 in a closed position. The top plate 54 provides a contact surface that abuts a corresponding contact surface of the bottom plate. A partial-pipe channel, typically a half-pipe channel, is formed co-extensively within each of the contact surfaces. A full-pipe channel 56 is formed when the top plate 54 is reversibly fastened to the bottom plate 52. Thus, the full-pipe channel 56 is formed when the catheter clamp 50 is in a closed position with a part of the channel defined by the contact surface of the bottom plate 52 and the remainder of the channel defined by the contact surface of the top plate 54.

The full-pipe channel 56 is sized to frictionally engage catheter 30 and is substantially co-axial with first aperture 24 and second aperture 28 so that capture of catheter 30 within full-pipe channel 56 maintains a substantially linear path for catheter 30 from first aperture 24 through the interior chamber of the housing 12 to the second aperture 28. Frictional engagement between the catheter 30 and full-pipe channel 56 may include a lining of rubber or other suitable material with a high friction coefficient on part or all of the length of the full-pipe channel 56. During operation, sheath handle 26 is clamped by first aperture 24 remaining fixed to housing 12, while catheter clamp 50 mounted on linear actuator 44 captures catheter 30 and thereby effects a linear motion of the catheter 30 relative to sheath handle 26.

Figure 4:
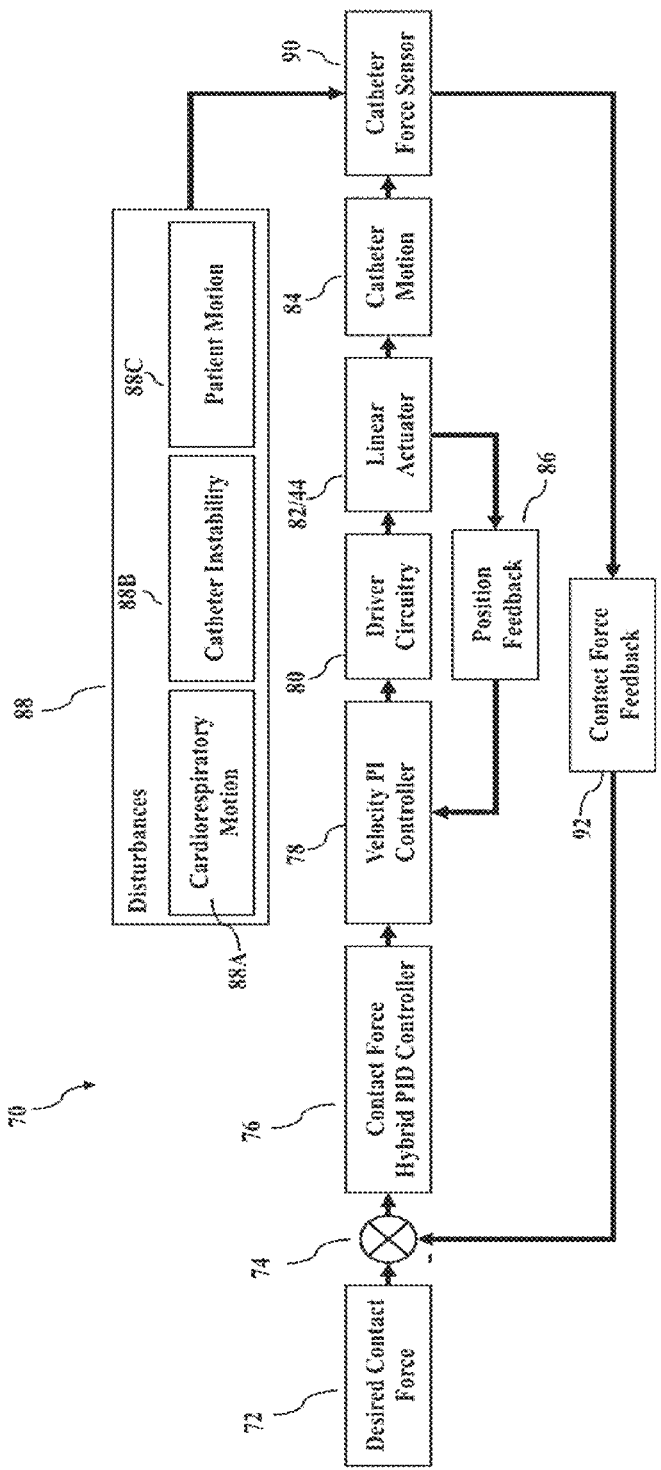
FIG. 4 shows a flow diagram for a system incorporating the CFC device 10 in (A) a first variant, (B) a second variant and (C) a third variant.
Figure 4:
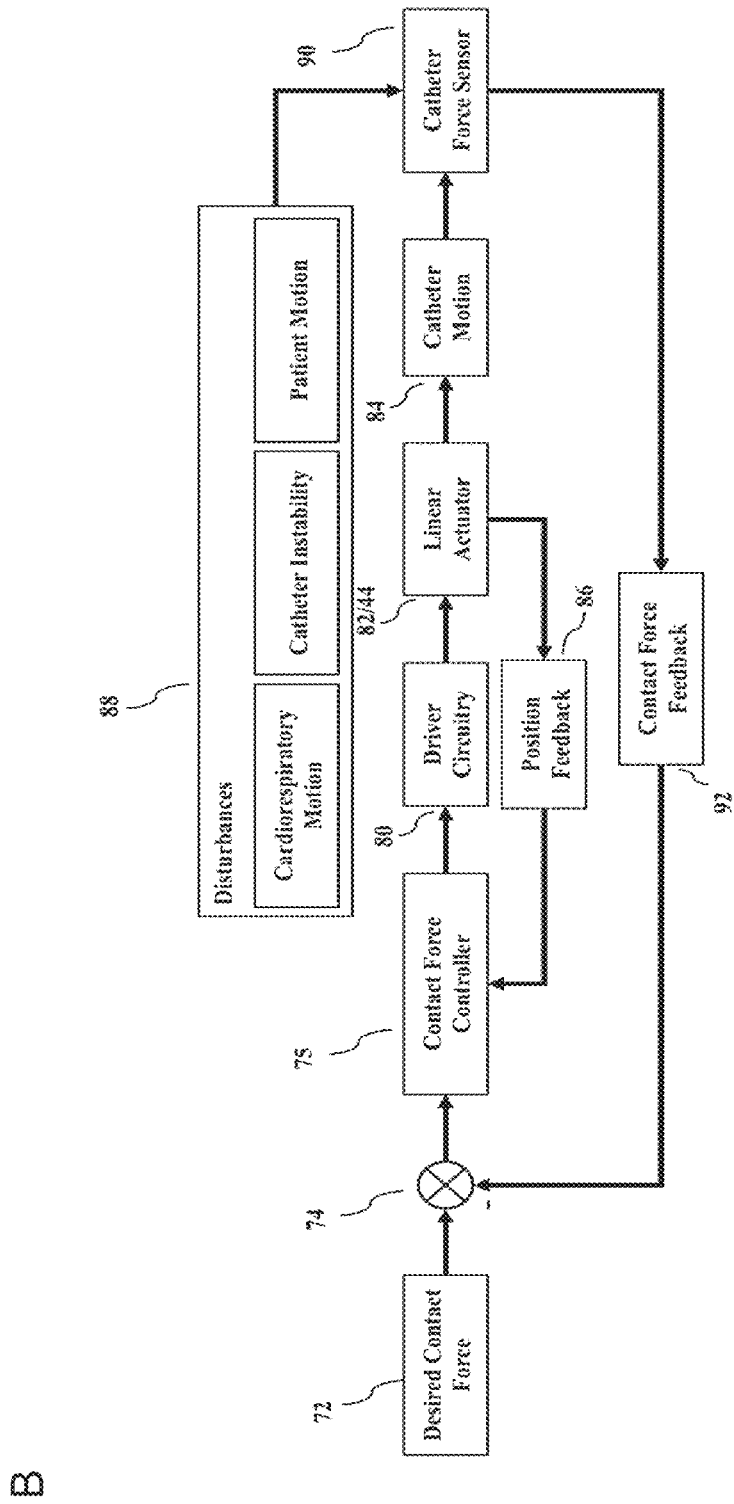
Figure 4:
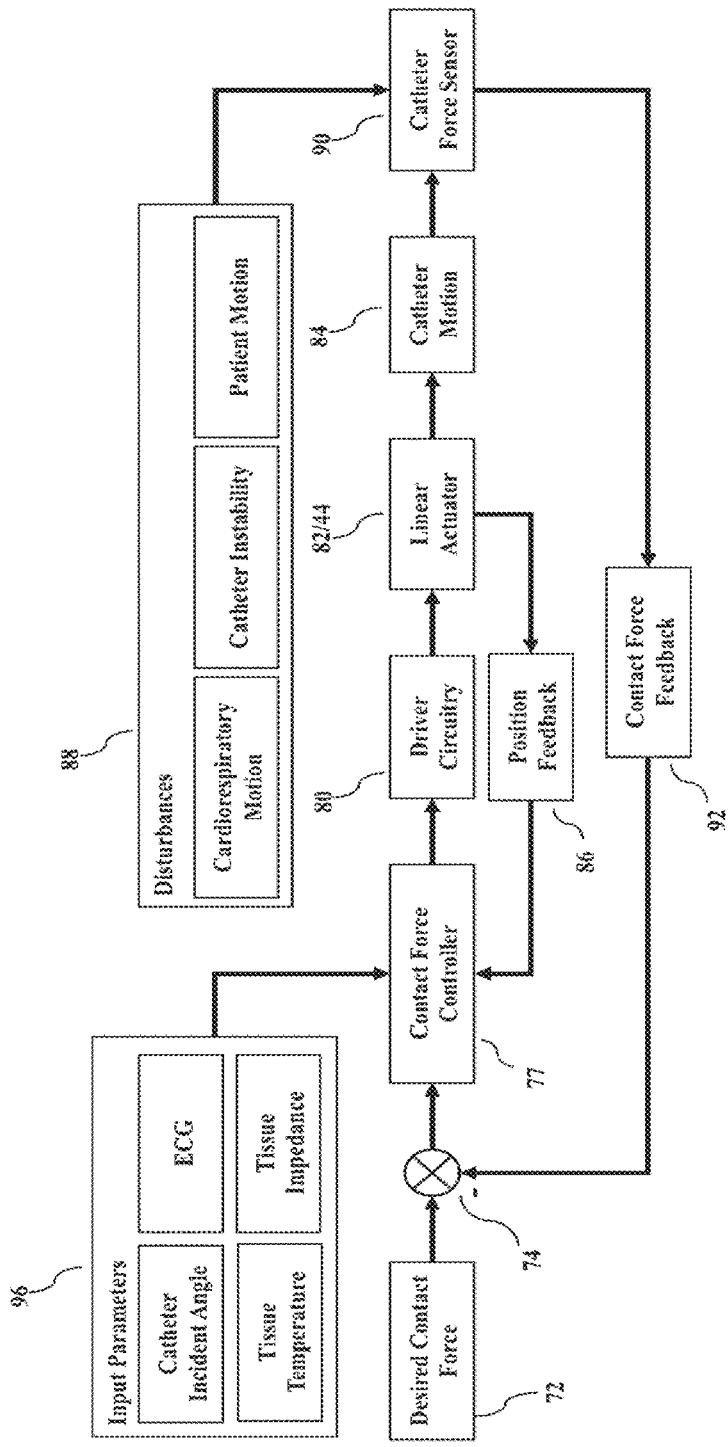

FIG. 4A shows a flow diagram of a cycle of a CFC system 70 incorporating the CFC device 10. Once a sheath 39 and catheter 30 are manually or robotically maneuvered so that a tip or remote end of the catheter 30 is at a target location the CFC device 10 is coupled to the catheter 30 and sheath handle 26 as shown in FIGS. 1 to 3 with both catheter clamp 50 and housing 12 in a closed position. The CFC system 70, and more specifically a hybrid proportional-derivative-integral (PID) controller 76 generates a pulse-width modulated (PWM) control signal referenced to a preset desired contact force 72. The PWM control signal is communicated to a velocity proportional-integral (PI) controller 78 that generates a control signal to control velocity of the linear actuator 44 based on the input PWM control signal. The control signal generated by PI controller 78 is communicated to driver circuitry 80 which in turn outputs the control signal with supply voltage and current that matches the requirements of linear actuator 44. Linear motion of linear actuator 82/44 is tracked using encoders and the position 86 of the linear actuator is communicated back to PI controller 78 to calculate change of position. Motion of the linear actuator 82/44 imparts motion to catheter 30 resulting in linear motion at the catheter tip 84. As the catheter tip touches the tissue a force sensor 90 measures the contact force between the catheter tip and target tissue. Disturbances 88 cause the force measured by contact force sensor 90 to change. Disturbances 88 include cardiorespiratory motion 88A, catheter instability 88B, and patient motion 88C. Contact force 92 is communicated in real-time to the hybrid PID controller 76 which executes a comparison 74 of the real-time contact force data 92 to the preset desired contact force 72 and begins a new round of the cycle by generating a new PWM control signal to minimize the difference between the real-time force data 92 and the preset desired contact force 72.

FIG. 4B illustrates a variant of the cycle shown in FIG. 4A where the position 86 of linear actuator 82/44 is directly fed back to contact force controller 75

FIG. 4C illustrates a variant of the cycle shown in FIG. 4B where additional input parameters 96 are fed to contact force controller 77 to provide additional arguments that influence the control signal fed to driver circuitry 80.

Figure 5:
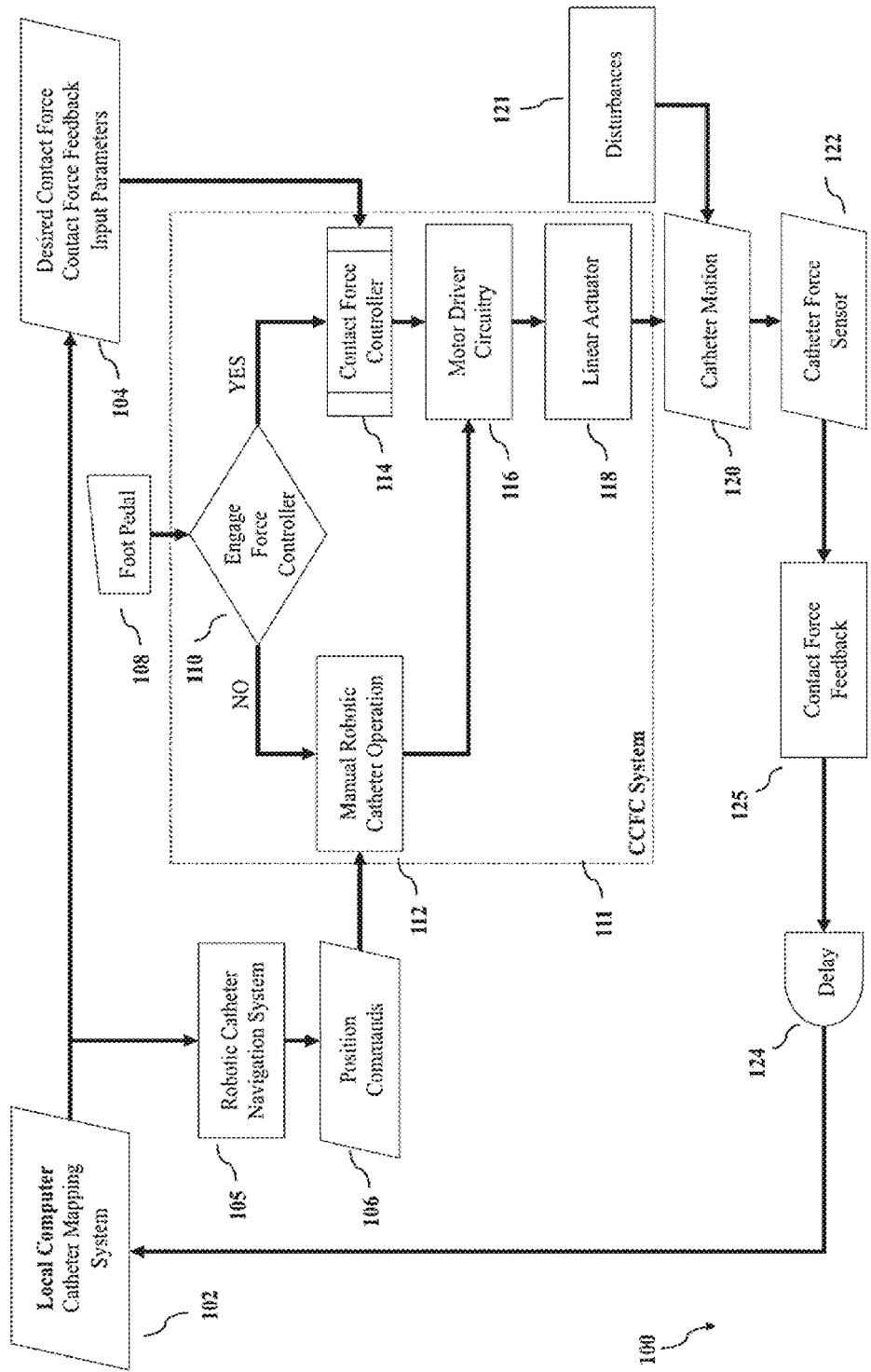
FIG. 5 shows a flow diagram for a modification of the system shown in FIG. 4A.

FIG. 5 shows an implementation of the cycle shown in FIG. 4A with the addition of a foot pedal 108 to control a start and stop of the cycle and an optional catheter robotic navigation system 105. The interventionalist can manipulate a catheter tip to a targeted location guided by a catheter mapping system represented in a graphic user interface installed and operating on a local computer 102. The sheath 39 may be manipulated manually by sheath handle 26 to position catheter 30 to the target location. Once at the target location the CFC device 10 can be coupled to the catheter 30 and sheath handle 26. Optionally, a robotic catheter navigation system 105 may advance catheter 30 through sheath 39 to the target location, by relaying position commands 106 to CFC 111. While the force controller is not engaged 110, CFC 111 permits manual robotic catheter operation 112. To engage 110 the CFC system 111 the foot pedal 108 is pressed resulting in catheter control force controller 114 generating a control signal to minimize the difference between real-time contact force and preset desired contact force 104. The contact force controller 114 can be any of controllers 75, 76, or 77. Input parameters 104, such as catheter incident angle, ECG, tissue temperature or tissue impendence, may also be an input for generation of the control signal. The control signal is outputted to the motor driver circuitry 116 which communicates the control signal to the linear actuator 118 with suitable supply voltage and current that matches the operational requirements of the linear actuator 118. Linear motion of the linear actuator 118 effects a corresponding linear motion of the catheter 120 providing a contact between the catheter and the target tissue and providing a new contact force data point detected by force sensor 122. Disturbances 121 may vary contact force. The new contact force data point 125 is communicated to local computer 102 which in turn communicates the data point to controller 114 to start the cycle over again. If the foot pedal is disengaged, the linear actuator and the catheter are retracted to a reference position. A serial communication protocol enables communication between the controller and a local computer. Optionally, with the foot pedal 108 disengaged the interventionalist may robotically move the catheter to a desired position 106 using a robotic catheter navigation system 105.

Figure 6:
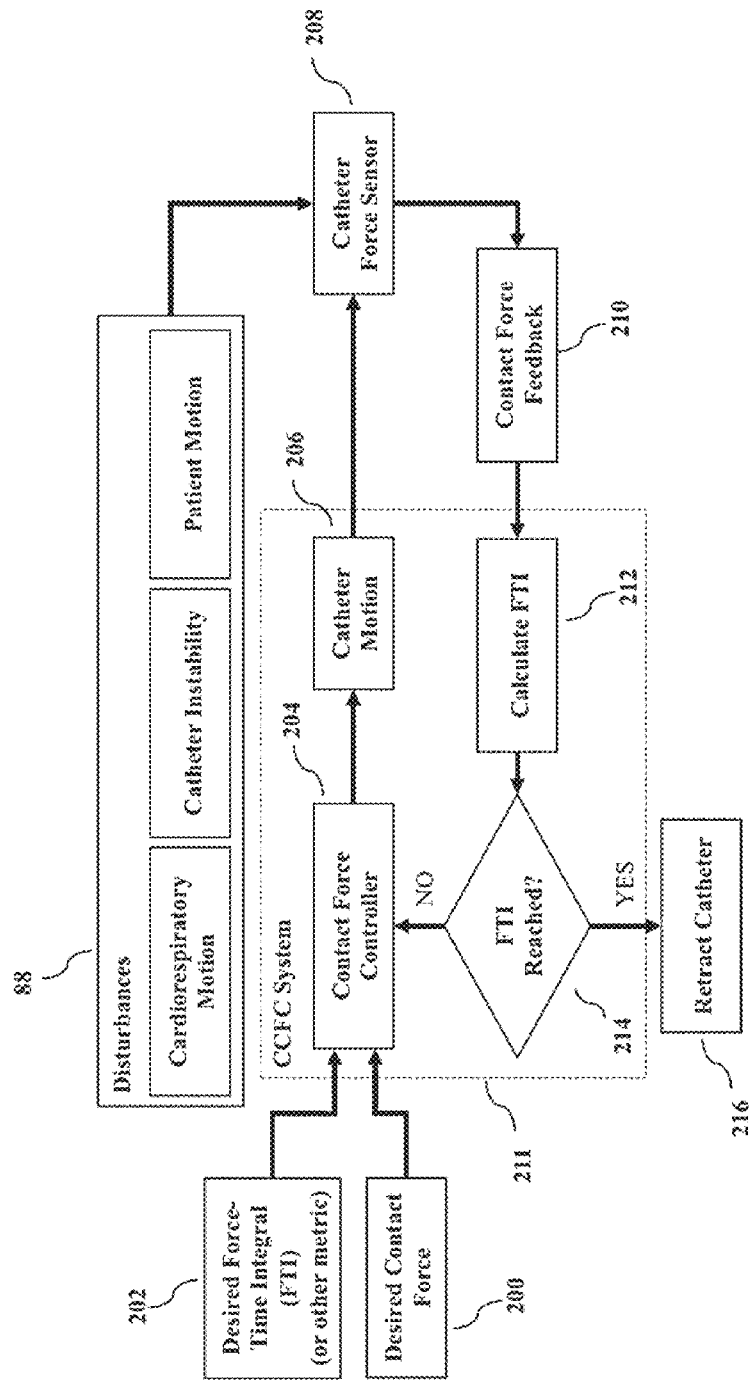
FIG. 6 shows a flow diagram for a fourth variant of a system incorporating a CFC device.

FIG. 6 shows a variant of the CFC system engaged to deliver a desired contact force 200 to the target tissue until a desired force time integral (FTI) 202 or other lesion size metric is reached. The catheter contact force controller 204 engages catheter motion 206 through the sheath 39 onto the target tissue. The new contact force data point 210 is communicated to CFC system 211. CFC system 211 calculates cumulative FTI 212 and compares 214 with desired FTI 202. If desired FTI 202 is not reached, the contact force controller 204 generates a new control signal and starts the cycle over again. When the desired force time interval 202 is reached in comparison 214 the catheter 30 is withdrawn back into the sheath 39 to a reference position. The contact force controller 204 can be any of controllers 75, 76, or 77.

The CFC device provides several advantages in a clinical setting. For example, the CFC device is a convenient hand-held tool that provides the ability to deliver ablation lesions in an optimal and controlled manner. Currently, there are no commercial devices that enable contact force control of the catheter tip. As another example, the CFC device can be readily retrofit with existing commercially available catheter systems. The CFC device can be an additional tool to standard catheterization procedures using off-the-shelf catheters and sheaths across multiple catheter manufactures. This feature of the device is advantageous as there is no need for specialized proprietary instruments and does not require the redesign of infrastructure of the operating room, which is often the case for catheter robotic systems. As yet another example, the CFC is completely compatible as an add-on device with manual intervention; it can be added after the interventionalist has inserted the sheath and catheter into the vascular system, can be removed at any time and subsequently repositioned without compromising the sterility of the sheath and catheter.

The successful use of the CFC device has been demonstrated experimentally to show a desired contact-force control between a catheter tip and a target surface. Illustrative experimental demonstrations of the CFC device are now described.

Percutaneous radiofrequency (RF) catheter ablation is becoming the standard of care for a variety of cardiac arrhythmias. Cardiac interventionalists introduce ablation catheters into the heart and manipulate them until the distal tip contacts the targeted myocardium. Once reached, RF power is delivered to form ablation lesions that interrupt the electrical pathways responsible for the arrhythmia. For successful treatment it is important that these lesions are transmural, as superficial lesions leave areas of healthy myocardium that may result in conduction recurrence and ablation failure.

Catheter-tip-to-tissue contact force (CF) has been shown to be an indicator for assessing lesion development, and CF guidelines have been established to label a delivered lesion as effective. Additional studies have shown that monitoring both the duration of the delivery and CF at a specific RF power can predict lesion volume. Conventionally described as a Force-Time Integral (FTI), the model may be used as a prospective quantitative tool to determine lesion volume under defined parameters. Unfortunately, this model is dependent on catheter stability and while used in the clinic as a guide, it has not been used as a quantitative metric that can predict lesion volume or transmurality. Finally, lesions delivered with excessive CF present a risk of deep tissue overheating, which may result in "steam pop", perforation and injury outside the heart, including esophageal, pulmonary and phrenic nerve damage. These potential risks often inhibit the interventionalist and cause them to deliver the lesion tentatively, with a lower level of CF to lessen the risk of injury. Clinically, CF information is often used as a guide to ensure catheter tip contact and confine the CF within acceptable ranges, but is ultimately limited by tissue motion, as seen in the CF profile in the lower right-hand corner of FIG. 1.

While ideally the CF should be regulated within a prescribed range, interventionalists cannot respond fast enough to compensate for cardiac and respiratory motion. Approaches to minimize myocardial motion during ablation, have been proposed, including high-frequency-jet ventilation. None have successfully provided a motionless environment in all patients.

Commercial force-sensing ablation catheters enable the interventionalist to simultaneously monitor the CF in real-time while delivering the lesion. Often these catheters are used together with steerable sheaths, whose added level of versatility and stability has increased clinical success. The interventionalist typically manipulates the steerable sheath until the catheter is pointing at the target region, and then advances the catheter forward through the sheath until the desired level of CF is imparted onto the tissue.

Hand-Held Device. The hand-held CFC device is mechanically clamped to the distal end of the sheath handle (i.e. at the hemostatic seal and insertion point of the catheter). A catheter-locking adapter rigidly clamps the catheter shaft onto a precision linear actuator (LM2070-040, MICROMO, Clearwater, USA) traveling along a 12 mm diameter 134 mm long precision magnetic shaft. Movement of the actuator directly translates to movement of the catheter through the sheath. The adapter and actuator are mounted within an enclosure, which is designed to securely lock onto the sheath handle, while keeping the catheter concentrically mounted within the hemostatic seal. A set of hinges and latches enables easy clamping and removal of the CFC. Both the adapter and enclosure were fabricated in polypropylene using additive manufacturing (Objet3D Pro, Stratasys Ltd., Rehovot, Israel).

Hybrid Control System. A hybrid control system maintains a prescribed CF between the tip of the catheter and a moving target. Common closed-loop proportional-integral-derivative (PID) control algorithms are based on minimizing the error between the desired and actual inputs, and have been shown to be a viable solution in robotic catheter control systems. The CFC uses a hybrid PID controller, a slight variation of a standard PID controller, whose control parameters change based on the error argument. The control signal u(t) is calculated as:

$$u(t) = \begin{cases} K_{P_A}e(t) + K_{I_A}\int_0^t e(\tau)d\tau + K_{D_A}\frac{d}{dt}e(t) & e(t) > F_T \\ K_{P_C}e(t) + K_{I_C}\int_0^t e(\tau)d\tau + K_{D_C}\frac{d}{dt}e(t) & 0 < e(t) \le F_T \end{cases}$$

where the error e(t) is the difference between the desired and current contact forces, $F_D$ and $F_C(t)$ respectively. The control parameters $K_P$, $K_I$ and $K_D$ generate a different control signal depending on the error measured in real time. If the error is larger than a predefined CF threshold, $F_T$, the control system is in an "aggressive" state indicated by $K_{PA}$, $K_{IA}$, $K_{LA}$. When the error is lower than $F_T$ the control system operates in a "conservative" state indicated by $K_{PC}$, $K_{IC}$, $K_{DC}$. The CF threshold was empirically assigned to be 5 g—a level that was observed to retain steady-state accuracy. Tuning of the aggressive control parameters was achieved using the Tyrues-Luyben tuning method (B. D. Tyreus, and W. L. Luyben, "Tuning PI controllers for integrator/dead time processes," Industrial & Engineering Chemistry Research, vol. 31, no. 11, pp. 2625-2628, 1992). The conservative control parameters were manually tuned for a desired steady-state response; in the current implementation, the conservative control parameters were at least a factor of 4 smaller than the aggressive ones.

Electronic Hardware Design. The hybrid control system was implemented within an embedded electronic system, enabling real-time control of the linear actuator. A microcontroller development platform based on a Atmel SAM3X8E 84 MHz 32-bit ARM architecture (Due, Arduino LLC, Ivrea, Italy) generates a pulse-width modulated (PWM) control signal, based on the measured and desired contact force, which acts as input to the linear actuator controller and driver circuitry (MCLM-3003, MICROMO, Clearwater, USA). This daughter board is programmed with a native velocity proportional-integral (PI) controller that controls the speed of the motor based on the input PWM signal. Tuning of the PI controller was performed using the manufacturer's tuning software, before tuning the hybrid PID system. The update rate of the hybrid PID system was set to 1 kHz, which was the maximum rate of the linear actuator controller.

Figure 7:
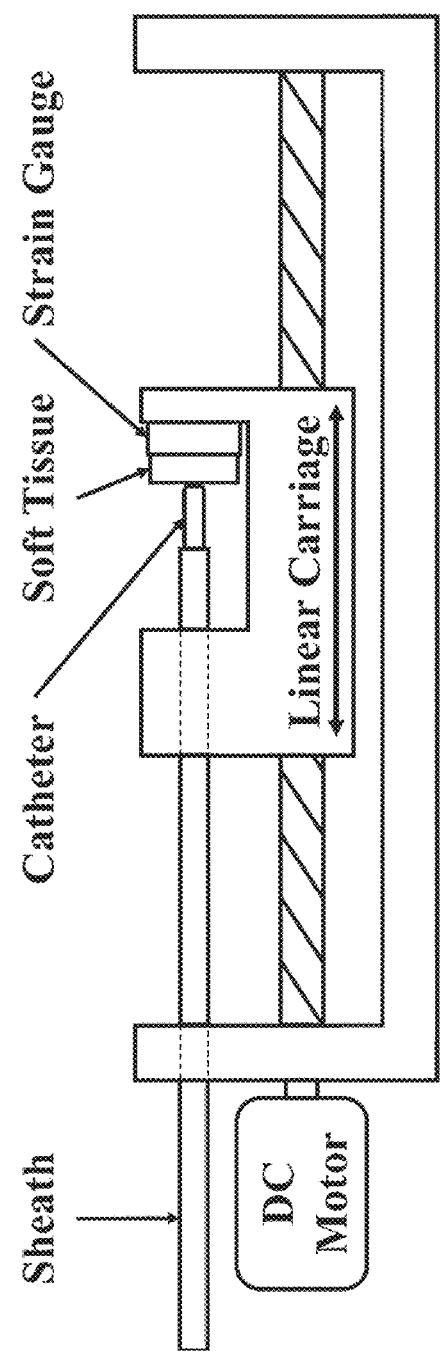
FIG. 7 shows a schematic view of a linear motion phantom with a catheter and sheath loaded, used to evaluate the CFC device.

Linear Motion Phantom. To evaluate the CFC's ability to regulate CF on a moving target in vitro, a custom built linear motion phantom was developed (FIG. 7). The motion phantom was built to provide sinusoidal and physiologic motion profiles. A gear motor with a Hall effect encoder (37D Gearmotor, Pololu Electronics, Las Vegas, NV, USA) drives a lead screw mechanism providing linear motion to a carriage. A second PID control system within an embedded electronic system controls the motion stage: the circuit board assembly includes a microcontroller development platform (Due, Arduino LLC, Ivrea, Italy) and a DC motor driver daughter board (VNH5019 Driver Shield, Pololu Electronics, Las Vegas, NV, USA). A strain gauge capable of detecting force with 200-milligram resolution (S100, Strain Measurement Devices, Wallingford, CT, USA), coupled to a linear amplifier (CSG110, FUTEK Inc., Irvine, CA, USA), is mounted on the carriage and used to measure the CF of the tip of the catheter. A piece of silicone (Dragon Skin 30, Smooth-On Inc., Macungie, PA, USA) is positioned between the strain gauge and the tip of the catheter to mimic soft tissue compliance. A setscrew fixes the sheath firmly in place without hindering movement of the catheter housed within the sheath. Linear calibration, according to Hooke's law, was first performed to determine the relationship between the displacement of the tissue and the force measured by the strain gauge. The phantom was programmed to execute arbitrary sinusoidal and sine-sweep motion profiles and to replicate physiological motion. Contact force profiles were recorded by force-sensing ablation catheters during typical ablation procedures, similar to the profile illustrated in FIG. 1. These profiles, containing both high-frequency low-amplitude cardiac and low-frequency high-amplitude respiratory motion, were programmed into the motion phantom as position trajectories, using the linear calibration parameters. The signal from the strain gauge, measured in real time, was used as the CF feedback signal of the CFC control system and represents a surrogate of the CF signal that would be provided by a commercial force-sensing catheter.

Linear Motion Phantom Evaluation. The linear motion phantom was first evaluated to ensure that the executed motion profiles mimic the physiological motion that results in contact force profiles similar to those measured clinically. The catheter was held fixed while the linear motion phantom imposed 16 different patient-specific motion profiles. The sheath was locked in place for half of the experiments. The real-time CF measurements provided by the strain gauge were recorded and compared to the corresponding CF profiles. No attempt was made to perfectly match the executed CF profiles to the corresponding patient profiles and the measured CF profiles were only inspected visually, ensuring the range of amplitudes and frequencies were within the physiologic range.

Figure 8:
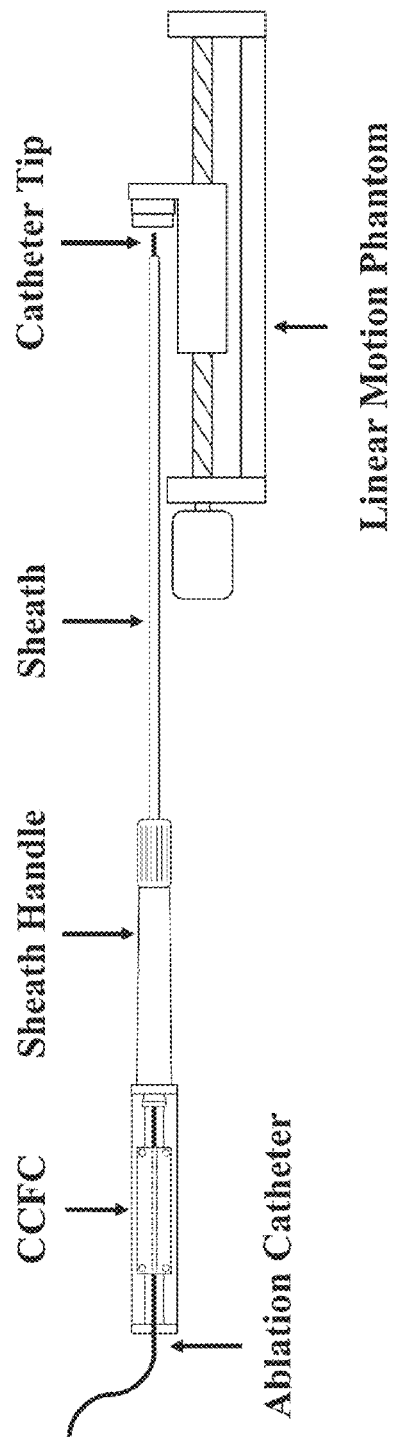
FIG. 8 shows a schematic view of the CFC device, sheath and catheter mounted with the linear motion phantom.

Catheter Force Controller Evaluation. Experiments were performed to evaluate the overall accuracy and dynamic performance of the CFC. For these experiments, the CFC was attached to the rear end of a commonly used steerable sheath (8F Agilis NxT, St. Jude Medical, Saint Paul, MN, USA) and CF sensing ablation catheter (7.5F SmartTouch, Biosense Webster Ltd., Diamond Bar, CA, USA) combination. Water was introduced via the sheath's side port to mimic the clinical setting and reduce the friction between the sheath and catheter. The sheath and catheter were inserted into the linear motion phantom as illustrated in FIG. 8.

1) Step Response: The response of the CFC control system to a step input (of 25 g) was first evaluated. The step response was then measured during 25 repeats and the rise time, overshoot, and peak level were characterized. During these experiments, the linear motion phantom was kept fixed.

2) Safety: The CFC was tested for response to excessive, fast and sudden motions that may result in tissue perforation. The linear motion phantom was programmed to impose a bidirectional continuous sine sweep motion profile, sweeping from 0.1 Hz to 2.5 Hz with amplitude of 70 g peak-to-peak. This unlikely clinical scenario was selected following Fourier analysis of over 40 patient-specific CF profiles and determining that the maximum frequency component observed was 2.5 Hz. While the phantom executed the prescribed motion, the CFC was engaged and attempted to regulate the CF to a desired reference of 25 g. The maximum error between the desired and actual contact force was measured. This experiment was repeated 10 times.

3) Patient-Specific Dynamic Response: To evaluate the overall performance of the CFC versus manual intervention, the linear motion phantom was programed to execute 16 different patient motion profiles. Prior to any evaluation of the CFC, a control experiment was performed whereby the phantom replicated each profile with the CFC's disabled. This is representative of manual intervention, where the interventionalist contacts the catheter to moving myocardial tissue and holds the catheter still to deliver a lesion. The experiment was then repeated with the CFC programmed to deliver 15 g, 25 g, and 40 g for the duration of the motion profile. Statistical analysis of the regulated CF profiles was performed to calculate mean, confidence interval, and root-mean-squared error (RMSE). Histograms of CF were also plotted for the "manual" and CFC interventions. Note that for this study we use the term "manual" to refer to the CF profile representative of CF profiles recorded during clinical ablation procedures.

4) Force-Time Integral: This experiment was designed to demonstrate that the CFC could be used not only to regulate the delivered force, but also to deliver lesions with prescribed FTI. The CFC was programmed to deliver a prescribed FTI at a desired CF while the linear motion phantom imposed a patient motion profile. For each FTI/CF combination an expected duration can be calculated. The CFC was programmed to calculate the FTI, and automatically retract the tip of the catheter back into the sheath once the desired FTI was reached. The generated CF profile and duration of catheter engagement was recorded and compared with expected values. This experiment was then repeated for various configurations of FTI and CF, which may be user-defined in a clinical setting. The tested FTI values were 500, 1000, and 1500 gs, where each was repeated with 25 g and 40 g of CF. Each configuration was repeated 3 times.

Figure 9:
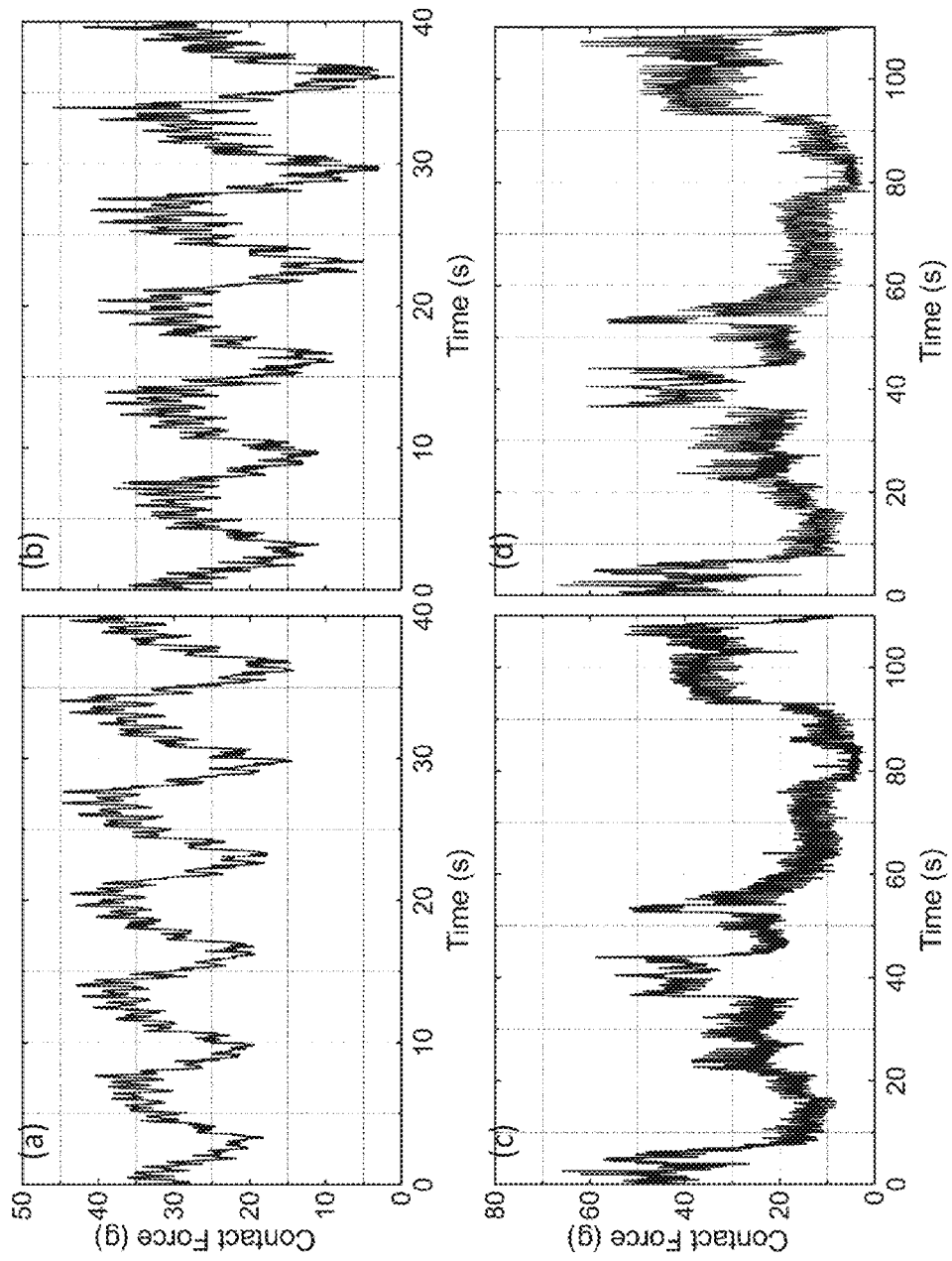
FIG. 9 shows two representative patient contact force (CF) profiles ((a) and (c)) and the corresponding CF profiles ((b) and (d), respectively) imposed on a fixed catheter tip by the linear motion phantom, executing the same patient profile.

Linear Motion Phantom Results. The linear motion phantom was able to replicate a range of patient-specific CF profiles. The profiles chosen to evaluate the CFC are characteristic of typical cardiorespiratory patterns depicted in FIG. 9($a$) as well as irregular profiles associated with patient motion or catheter instability depicted in FIG. 9($c$). The generated CF curves, shown in FIG. 9($b$, $d$), visually demonstrate a high level of similarity to the corresponding clinically acquired profiles (FIGS. 9 $a$ and $c$). These results demonstrate that the linear motion phantom is able to replicate cardiorespiratory forces that is typically encountered during catheter RF delivery and is appropriate to be used as a phantom for the CFC's evaluation. Locking the sheath in place did not affect the results.

Figure 10:
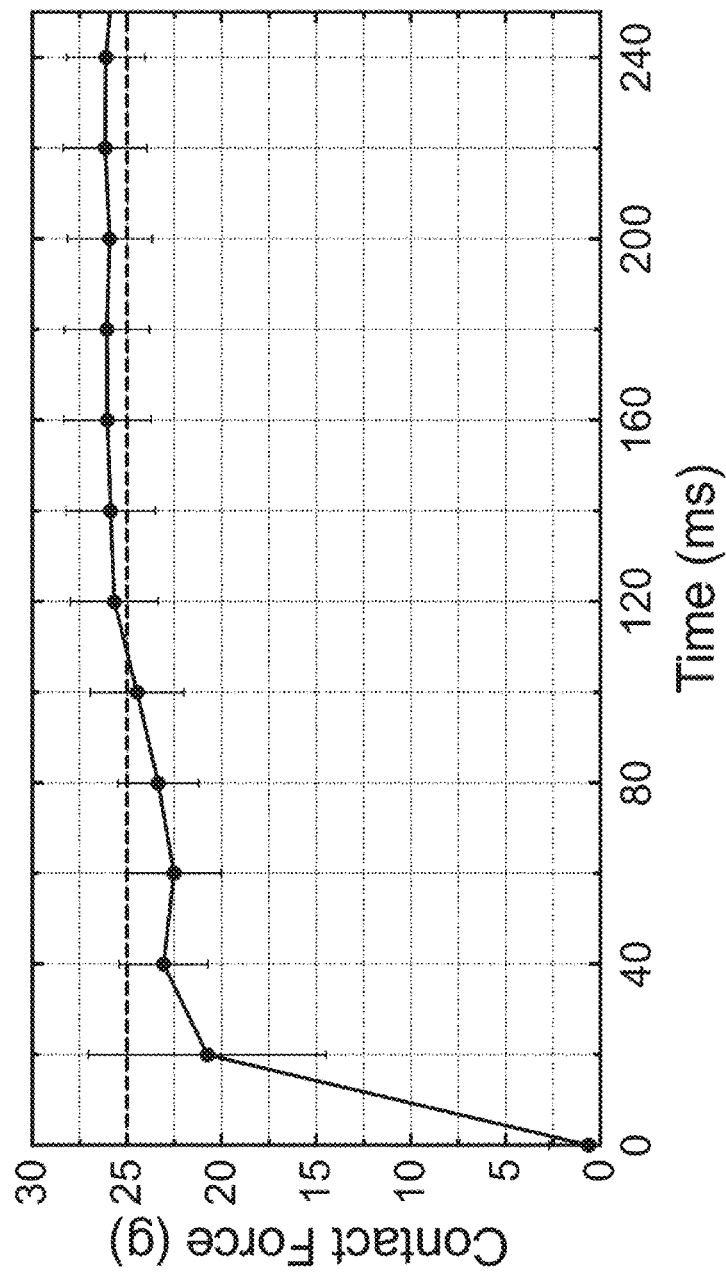
FIG. 10 shows a step response of the CFC device for a reference value of 25 g, with mean and standard deviation plotted at each time point.

CFC—Step Response—Results. The response of the CFC's control system to a 25 g step input is shown in FIG. 10. The following step response characteristics were calculated from the measurements: 38±3 ms rise time, 3±2 g overshoot, and peak of 29±2 g; means and standard deviations of 25 repeats of the step response are reported. The negligible overshoot and oscillation indicate that the tuning method used to determine the control parameters has resulted in a desired transient and steady state response.

CFC—Safety—Results. During the control of a 70 g peak-to-peak sine sweep from 0.1 Hz to 2.5 Hz, the maximum difference between the prescribed and measured CF was 15±2 g, with all measured CF values being below 42 g. These results demonstrate that the CFC is capable of reacting to sudden changes of tissue displacement that would otherwise result in large spikes of CF and potentially cause tissue damage.

Figure 11:
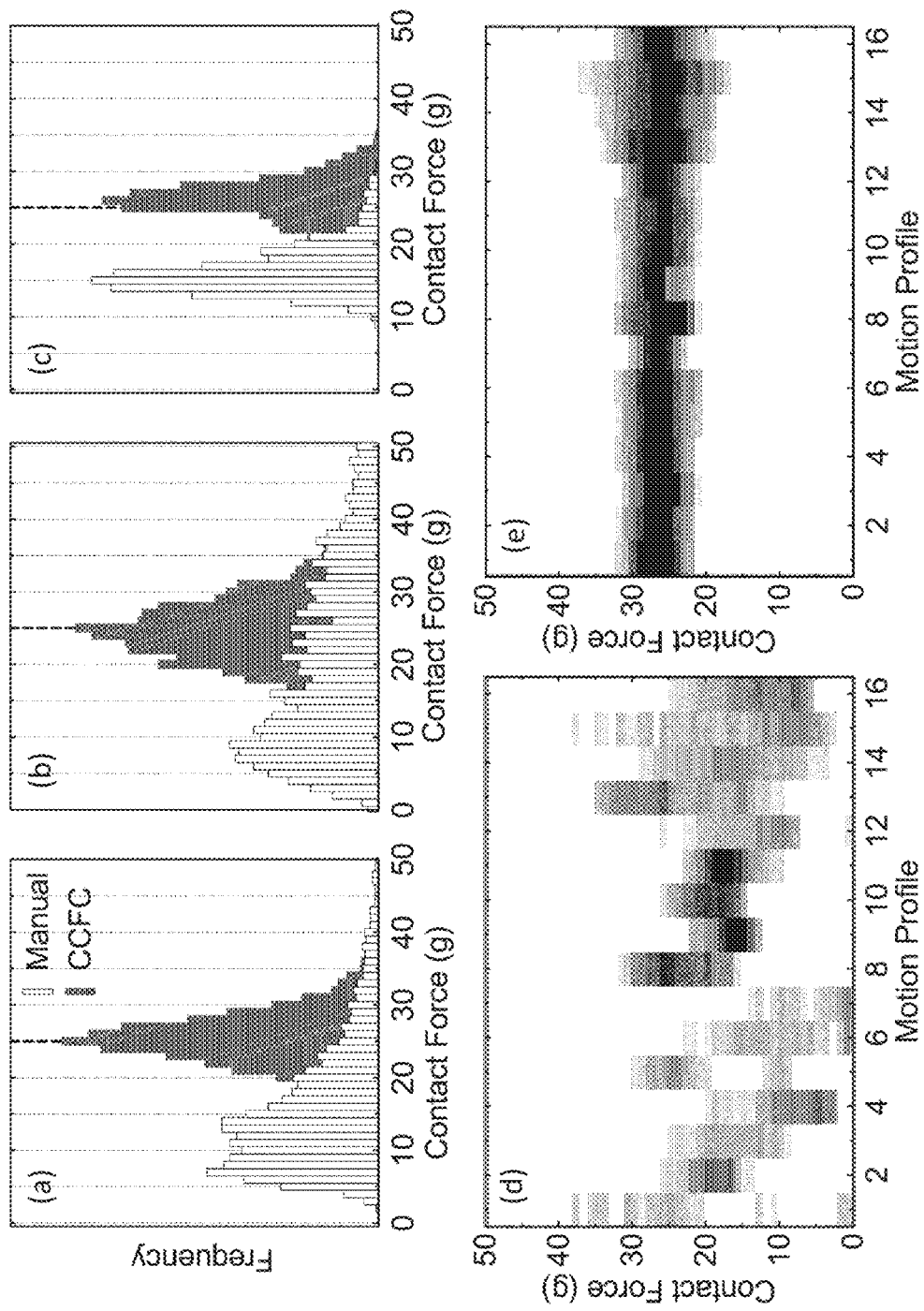
FIG. 11 shows histograms (a)-(c) of the distribution of manual and CFC-controlled CF for three unique motion profiles (16, 15, and 9 from panel (d), respectively), and grey-scale representations of 16 manual (d) and 16 corresponding CFC-controlled (e) interventions (motion profiles in FIGS. 9 (b) and (d) are profile #13 and #3, respectively in panel (d))
Figure 12:
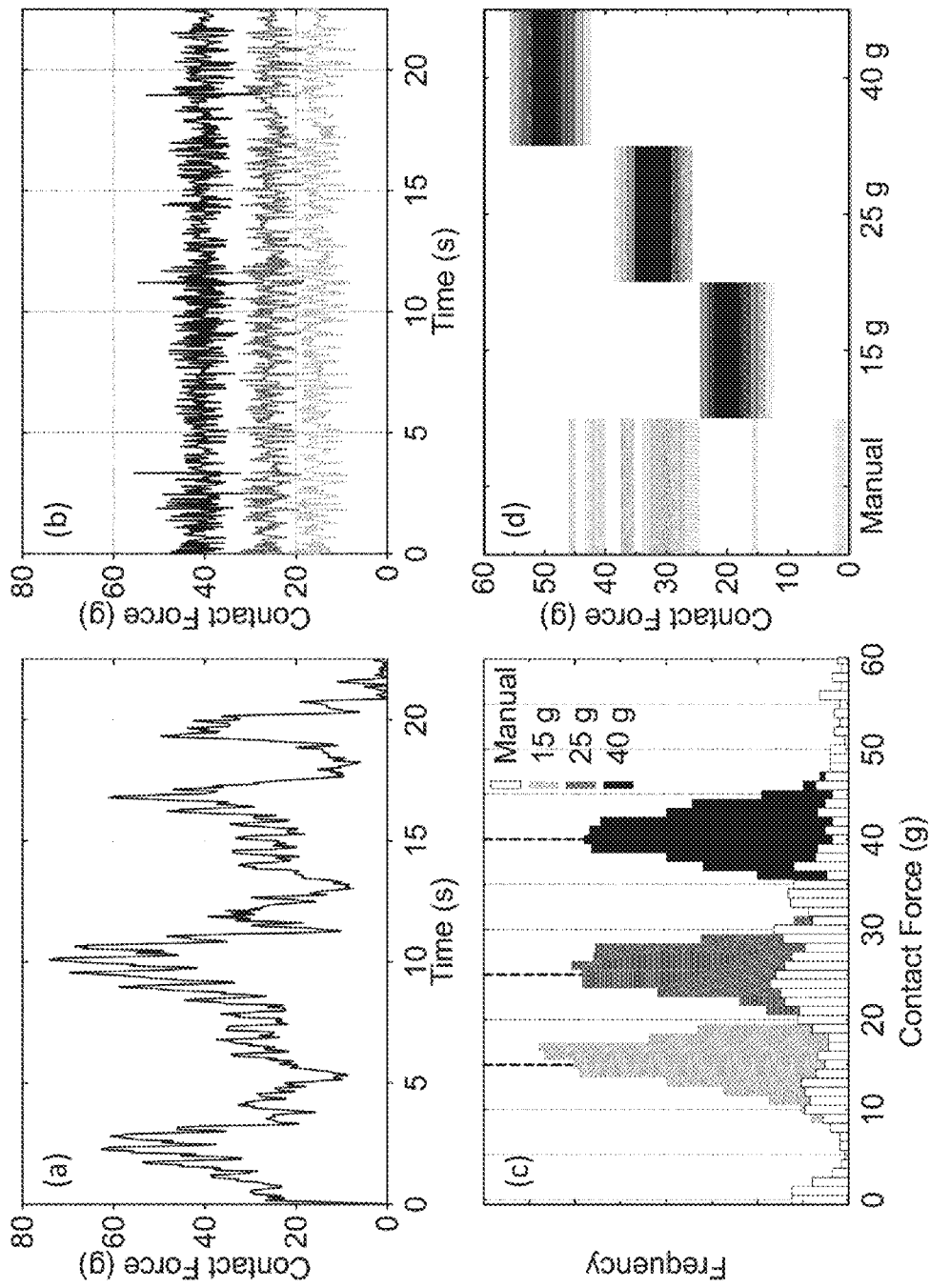
FIG. 12 shows (a) CF profile, while the CFC was disabled; (b) the generated CF profile while the CFC was engaged to deliver 15 g (bottom plot), 25 g (middle plot) and 40 g (top plot); and histogram (c) and grey-scale representation (d) illustrating the CF distribution between manual and CFC intervention at various desired CF levels (the motion profile corresponds to profile #1 from FIG. 8(d))

CFC—Patient-Specific Dynamic Response—Results. The CFC was able to significantly transform the CF profile on the catheter tip in comparison to manual intervention ($p<0.001$). FIG. 11($a$-$c$) depicts the distribution of measured CF for three motion profiles, representative of CFs measured during the delivery of different lesions; histograms are plotted for both manual and CFC-controlled interventions, with a prescribed CF level of 25 g. The images in FIG. 11($d$, manual) and FIG. 11($e$, CFC-controlled) are grey-scale representations of the CF histograms for all 16 motion profiles; they clearly demonstrate that when the CFC is engaged the prescribed mean force is achieved for all motion profiles. Similar performance was achieved regardless of the magnitude of the prescribed CF. Illustrated in FIG. 12, are the results for one representative experiment where the CFC was programmed to deliver a CF of three clinically relevant levels—15, 25, and 40 g. Consistently similar force distributions, were achieved regardless of the prescribed CF value. Detailed performance metrics—averaged over all tested motion profiles—are shown in Table I for the three prescribed CF levels.

TABLE I

PATIENT MOTION EXPERIMENTS

| Prescribed CF (g) | 15 | 25 | 40 |
|---|---|---|---|
| 5% Percentile | 10.1 ± 1.2 | 19.7 ± 1.2 | 34.3 ± 1.2 |
| 95% Percentile | 20.6 ± 1.3 | 31.1 ± 1.5 | 46.9 ± 1.7 |
| Mean | 15.3 ± 0.1 | 25.4 ± 0.1 | 40.4 ± 0.1 |
| RMSE | 3.2 ± 0.6 | 3.4 ± 0.7 | 3.9 ± 0.8 |

Figure 13:
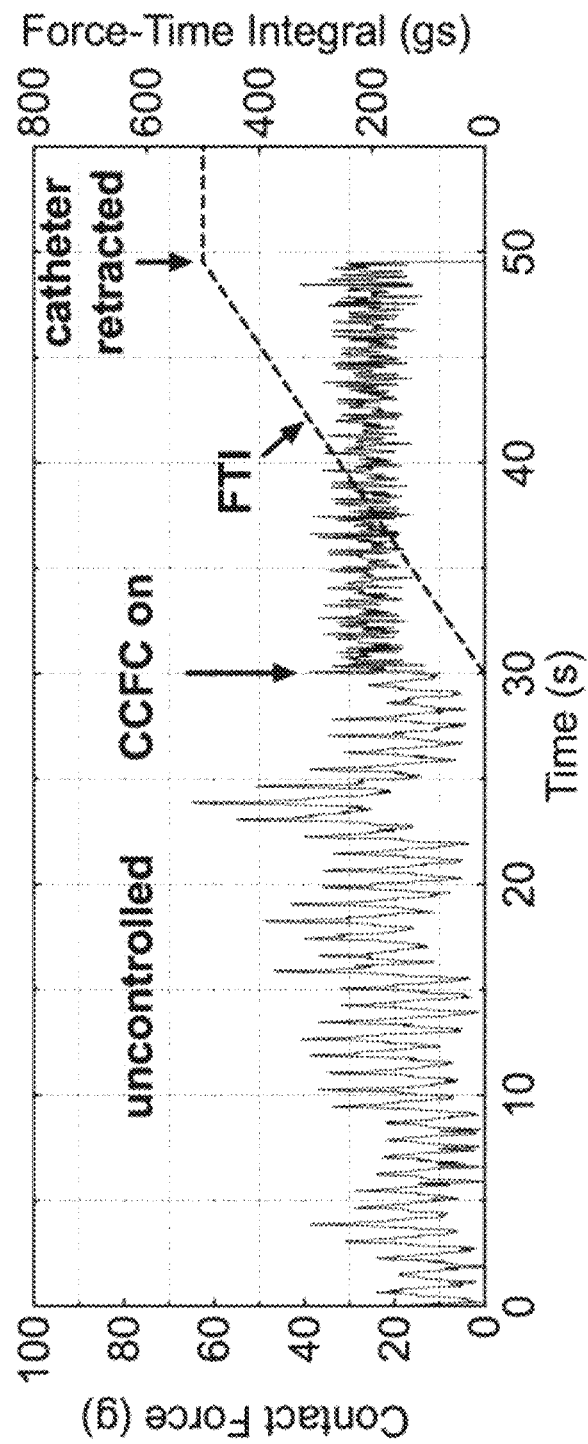
FIG. 13 shows CF profiles for interval 0-20 s (the catheter in contact with the phantom while the CFC was disabled), interval 20-39.5 s (the CFC engaged to deliver 500 gs at 25 g) and interval 39.5-45 s (the tip of the catheter retracted into the sheath once the desired FTI (dashed line) had been reached), the motion profile corresponding to profile #15 from FIG. 8(d).

CFC—Force-Time Integral—Results. For all experiments performed to demonstrate that the CFC could achieve a target FTI, the CFC successfully engaged the catheter with a desired CF until a target FTI was reached. The results obtained with each configuration of FTI and CF are presented in Table II. A representative experiment is illustrated in FIG. 13. The lesion delivery time was within 480±199 ms of the expected duration. This is indicative of a regulated CF profile throughout the delivery, as excessive CF would result in short lesion delivery times and low CF levels would result in the opposite. With each configuration of desired CF and FTI a similar profile was generated with an expected and predicable deviation.

TABLE II

FORCE-TIME INTEGRAL EXPERIMENTS.

| Desired | | Expected | Measured | | |
|---|---|---|---|---|---|
| FTI (gs) | CF (g) | Duration (s) | FTI (gs) | CF (g) | Duration (s) |
| 500 | 25 | 20 | 500 | 25.7 ± 3.0 | 19.49 ± 0.01 |
|  | 40 | 12.5 | 500 | 40.7 ± 3.5 | 12.29 ± 0.01 |
| 1000 | 25 | 40 | 1000 | 25.4 ± 3.1 | 39.36 ± 0.04 |
|  | 40 | 25 | 999 | 40.4 ± 3.4 | 24.71 ± 0.01 |
| 1500 | 25 | 60 | 1500 | 25.3 ± 3.0 | 59.27 ± 0.06 |
|  | 40 | 37.5 | 1499 | 40.4 ± 3.4 | 36.99 ± 0.22 |

The CFC is an easy to use tool that regulates the CF imparted by standard ablation catheters on moving tissue regardless of the type of motion imposed. The compact hand-held device is used with commercially available force-sensing ablation catheters and steerable sheaths, which are widely used in modern electrophysiology suites. The presented CFC utilizes the same tools and information available to the interventionalist but grants the ability to regulate CF and FTI.

While contact force measurement (at the tip of an ablation catheter) has been available to electrophysiologists for some time, it has been used primarily as a visual guide to determine if adequate contact has been made or if there is a risk of tissue perforation. The CFC has been demonstrated to control the force at the tip of the catheter to within a few grams of a prescribed force level.

The CF profiles, recorded during clinical ablation procedures, used to impart clinically relevant motion for evaluating the CFC and shown in FIG. 11 demonstrate some of the problems associated with ablation delivery. For example, profile #16 (FIG. 11(a)) represents a lesion where negligible force existed between the catheter tip and the wall during most of the time RF power was being delivered; when the CFC was engaged the mean CF was increased to 25 g, as prescribed. Similarly, the scenario depicted in FIG. 11(b) demonstrates large variations in contact force (manual) due to motion, which is corrected via the use of the CFC, reducing the RMSE (about 25 g) from 15.1 to 5.5 g. Even when a tight distribution of forces is achieved manually, as in FIG. 11(c), the mean CF may not be at a level sufficiently high for the delivery of a transmural lesion—use of the CFC in this case shifts the distribution of CF from being centered about 15 g to being centered about 25 g. Consistently narrow, and symmetric, distributions of CF were also achieved for different prescribed CF levels (FIG. 12, Table I).

Successful control of CF over the duration of lesion delivery also enabled control of FTI. Automatic engagement and retraction of the catheter for specified FTI at a desired CF has the potential to become a fundamental and powerful tool in the electrophysiology suite. While FTI has been proposed as a useful measure in predicting lesion transmurality and volume, without a device like the CFC FTI cannot be easily used as a metric clinically or in preclinical studies aimed at optimizing lesion delivery parameters.

The study evaluating the performance of the CFC under conditions of rapidly varying motion have also demonstrated that use of the CFC clinically has potential to minimize tissue damage due to excessive force. The CFC was able to compensate for changes in CF as fast as 700 g/s and maintain CF within 15 g of the prescribed values. These results are significant because they indicate that using the CFC, forces able to perforate tissue are not produced.

The CFC is a hand-held device that enables the interventionalist to engage it at any point during a complete ablation procedure, but is free to perform all other tasks as is done under current clinical practice. The CFC can easily be removed from the catheter/sheath assembly to ensure optimal catheter steerability and be re-clamped when a target location has been reached, just prior to RF power delivery. The device is versatile and can be used as a stand-alone CF control aid or can be incorporated with catheter robotic navigation systems for further improvements in position and force control.

An illustrative version and several variants of a CFC device and a system and method incorporating the same have been described above without any intended loss of generality. Further examples of modifications and variation are contemplated.

For example, any suitable type of clamp may be used to immobilize a sheath handle to the CFC device. Similarly, any suitable type of clamp may be used to fix the catheter to the linear actuator. In one example, the clamp for the catheter provides a reversibly closeable full-pipe channel lined or layered with a gripping material such as rubber or any other suitable material having a high coefficient of friction.

The sheath clamp may engage any portion of the sheath handle to immobilize the sheath handle to the CFC device including, for example, a neck, a tubular body or both the neck and the tubular body of the sheath handle. As shown in FIGS. 1 and 2, first aperture 24 can capture or clamp a neck of a tubular body when the housing 12 is in a closed position.

Figure 14:
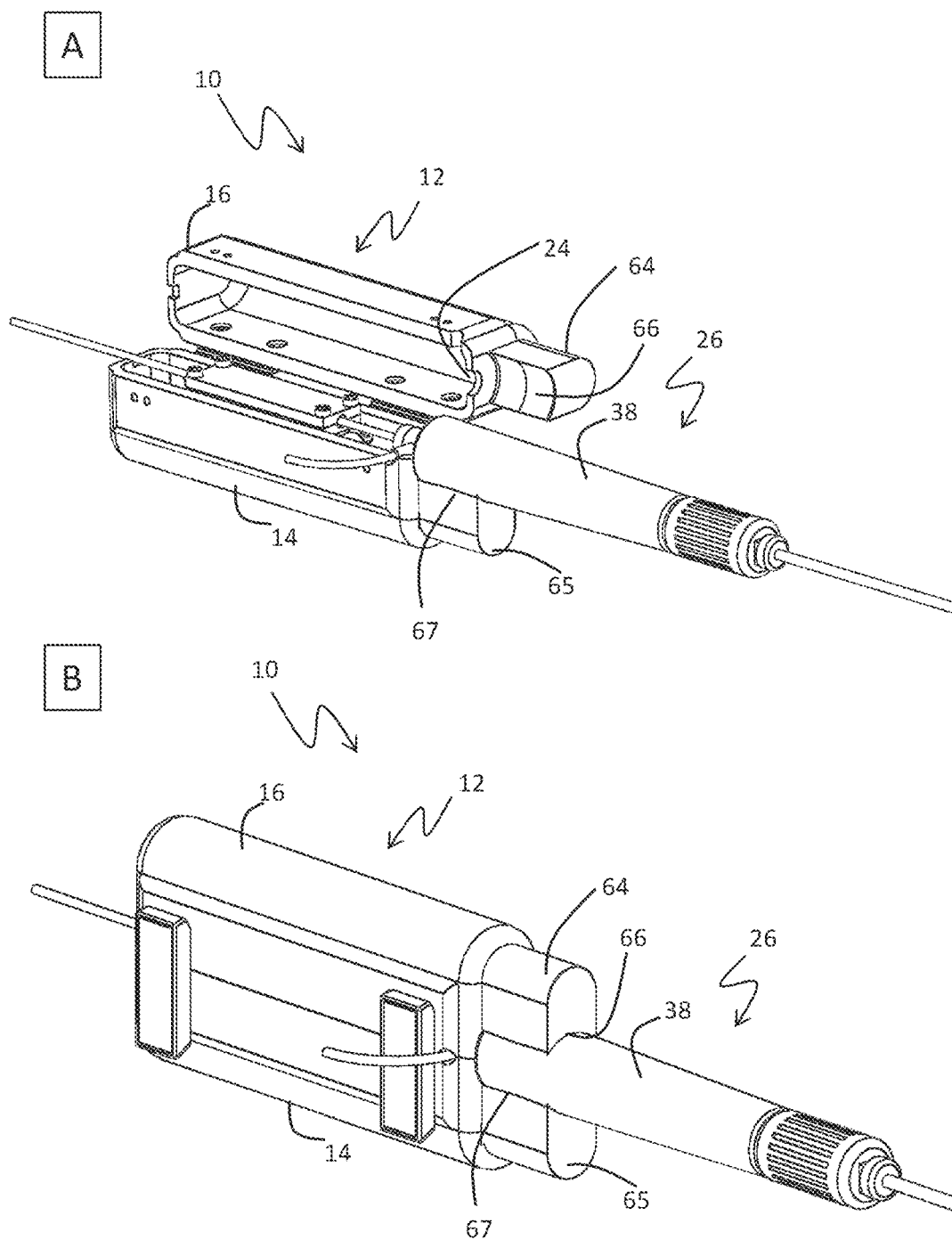
FIG. 14 shows an isometric view of a variant of the CFC device shown in FIG. 1 with the cover in (A) an open position and (B) a closed position.

Similarly, a clamp may be configured to capture the tubular body 38 of the sheath handle 26. For example, as shown in FIG. 14, a first jaw 64 may be connected or integrally formed with a longitudinal end of cover 16 while a second jaw 65 may be connected or integrally formed with a corresponding longitudinal end of base 14. The first jaw 64 provides a first mating surface 66 while the second jaw 65 provides a second mating surface 67. When housing 12 is in a closed position, the first mating surface 66 and the second mating surface 67 cooperate to engage radially opposed surfaces of the tubular body. The first and second mating surfaces may be texturized with surface features such as teeth, ridges, dimples, and the like to facilitate grip. The first and second mating surfaces may be formed of or layered with rubber or other suitable materials having a coefficient of friction that facilitates grip.

Sheath handles may be formed without the hemostatic seal shown, for example, in FIG. 1. Similarly, sheath handles may be formed without the neck structure shown, for example, in FIG. 1. Therefore, the sheath clamp may comprise first and second jaws 64 and 65 that cooperate to capture a tubular body of the sheath handle in addition to or instead of a sheath clamp that captures a neck structure of the sheath handle. The sheath clamp may incorporate any suitable type of clamp that effectively immobilizes the sheath handle relative to the housing of CFC device. Sheath clamps may not require connection to both the cover and the base and clamps connected to either the cover or the base may be sufficient. For example, a C-clamp fixed on a post extending from either the base or the cover may function as a sheath clamp. The post extending from the base or the cover is oriented parallel to the longitudinal axis of the housing and the sheath handle, while with the C-clamp is oriented transverse to the longitudinal axis of the housing and the sheath handle. With the C-clamp in an open position the sheath handle is positioned within the open ring defined by ends of the C-clamp, and then a toggled latch that closes and brings the ends of the C-clamp closer together can be used to tighten the clamp and capture the sheath handle. Similarly, a sheath clamp may comprise an O-shaped hose ring fixed on a post extending from either the cover or the base with a worm screw drive in threaded communication with the hose ring and operable to reduce or expand the diameter of the hose ring. Many other types of clamps are conventionally available and may be suitable to be included as a sheath clamp.

The sheath clamp may be substituted with any reversible connector or reversible fastener mechanism that allows the sheath handle to be removably coupled to the housing of the CFC device and functions to immobilize the sheath handle relative to the housing during operation of the CFC device.

The sheath clamp and the catheter clamp are typically aligned to be substantially co-axial so that during operation of the CFC device the catheter is maintained in a substantially co-axial alignment throughout the housing of the CFC device. However, deviation from co-axial alignment can be accommodated. Deviation from co-axial alignment will typically be less than about 30 degrees. Often deviation from co-axial alignment will be less than about 20 degrees. More often deviation from co-axial alignment will be less than about 10 degrees.

The linear actuator may be any suitable type and need not be limited to a sled and slide track mechanism. For example, the linear actuator may be a lead screw and lead nut with a rotary stepper or DC motor mechanism. In another example, the linear actuator may be a piezoelectric actuator or a voice coil.

The CFC device can accommodate any type of catheter including rigid or flexible catheters, needles or probes.

The CFC device may accommodate various controller types and controller algorithms to control contact-force of a catheter tip with a target tissue. For example, proportional-integrative-derivative (PID), proportional-integrative (PI) or proportional (P) algorithms may be used to control the CFC device depending on parameters of a specific implementation. Where PID algorithms are overwhelmed by time-delay in a system, various time-delay compensating algorithms are known that can be incorporated as desired depending on parameters of a specific implementation. For example, several time-delay compensating algorithms are described in: Control of Dead-time Processes, By J Normey-Rico, EF Camacho ch. 1 and 5; PID Controllers for Time-Delay Systems, By Guillermo J. Silva, Aniruddha Datta, Shankar P. ch. 1, 7, and 8; Industrial Digital Control System, By K. Warwick and D. Rees. ch. 5; www.mathworks.com/help/control/examples/control-of-processes-with-long-dead-time-the-smith-predictor.html; Industrial Digital Control System, By K. Warwick and D. Rees. ch. 10. Time-delay compensation can also be achieved by adaptive control algorithms as described, for example, in: Industrial Digital Control System, By K. Warwick and D. Rees. ch. 10; and Control of Dead-time Processes, By J Normey-Rico, EF Camacho ch. 4. Kalman Filtering can also be useful for time-delay compensation as described, for example, in: K. S. Walgama, "Control of Processes with Noise and Time Delays", AIChE, 1989, Vol 35, No. 2. Model Predictive Control (MPC) may also be useful for time-delay compensation as described, for example, in: Control of Dead-time Processes, By J Normey-Rico, EF Camacho ch. 9. Dahlin controller, which uses an internal model control technique (IMC) may also be useful for time-delay compensation as described, for example, at: web.stanford.edu/class/archive/ee/ee392m/ee392m.1056/Lecturell_IMC.pdf. Still further control algorithms are available that may benefit control of a process involving a time-delay or deadtime.

FIG. 15 provides flow diagrams of various illustrative controller algorithms that may be used to control the CFC device.

As represented schematically in FIG. 15A, proportional-integrative-derivative (PID) is a control loop negative feedback mechanism used universally in control applications. PID controllers calculate the error between the desired and measured contact-force, e(t), and apply a correction control signal, u(t), which is sent to the linear actuator of the device. As the linear actuator responds and translates the catheter through the sheath, a new contact-force reading is acquired and the loop repeats. The controller, C(s), is a PID transfer function relating the error and control signal to the motor, and the process, G(s), is a real world system relating the control signal to the motor and the resulting contact-force response. The closed-loop system compensates for output disturbances, including contact-force fluctuations caused by cardiorespiratory motion. While PID controllers provide a functional solution in many operating environments, a potential drawback to PID controllers is the sensitivity to time delay or deadtime, $\theta p$, in the control loop, which can lead to instability of control and diminish performance.

Control schemes are known that provide a means of alleviating the difficulty of controlling processes involving time delays. Such control schemes including, for example, a Smith Predictor, Gain-Adaptive PID, a Kalman filter or other suitable time-delay compensating algorithms may be incorporated to mitigate the effect of the deadtime in the control loop. As shown in FIG. 15B, the Smith predictor (SP) includes an ordinary feedback loop plus an inner loop that introduces a model of the process; the model of the process takes the form of a transfer function G(s), and an estimate of the deadtime, θpm. In this configuration, if $\hat{G}(s)=G(s)$ and θpm=θp, then the feedback yields an estimate of the disturbances without deadtime.

The real world process G(s) captures all the dynamics of the CFC device and the system used to control it. This includes, for example, the inertia of the motor, the compliance in the catheter, the compliance of the tissue, the dynamics of the force sensor, and the like. G(s) is a hidden relationship between the control signal to the motor and the output contact-force response. $\hat{G}(s)$ is a numerical model being processed on a microcontroller. This model can be developed using any suitable modeling software including, for example, a MATLAB (mathworks.com/products/matlab) black-box system identification method using input-output data.

Although the Smith predictor improves closed-loop performance in instances where deadtime is a significant concern, output disturbances with frequencies above $\theta_p^{-1}$ rad/s will not be reduced. In commercial force-sensing catheter systems, the amount of deadtime present in the system can prevent disturbance rejection of cardiac motion. As shown in FIG. 15C, an improvement to the Smith predictor control system may be introduced, where, an extra deadtime term $\theta_m$, is introduced, which further delays the feedback.

The extra delay is calculated as θm=T−θpm, where T is the period of the heartbeat of the patient. For instance, if the deadtime of the system is 0.1 seconds and the heartbeat of the patient is 75 BPM (0.8 seconds), then θm equals to 0.7. This calculation assumes that the heartbeat does not significantly fluctuate (since the majority of catheter ablation procedures use pacing techniques this assumption is fulfilled in the clinic). The linear actuator is now synchronized with the heartbeat delayed by one full cardiac cycle in addition to the deadtime. This results in a compensation of the cardiac disturbances. The heartbeat of the patient may be entered manually as an input to the control system or using an automatic method of determining the cardiac frequency component in the contact-force system. One such method includes pitch detection, which uses autocorrelation and peak detection to determine the cardiac frequency. This value is then used to automatically update the value of T.

For respiratory-motion-dominated targets in the heart, another modification to the Smith predictor may be introduced. Rather than further delaying the feedback, a filter F(s) is introduced, as shown in FIG. 15D. F(s) takes the form of a low-pass filter designed to remove high-frequency cardiac disturbances from the feedback pathway.

FIG. 15E shows a controller scheme that implements both cardiac compensation (SP with θm) and respiratory compensation (SP with F(s)) algorithms. The components shown within the boundaries of the dotted line are processed in real-time on a microcontroller. Switching between the two control algorithms can be either manual or automatic. For instance, if the physician is manipulating a catheter to a target and notices that the contact-force profile is dominated by cardiac motion, the cardiac compensation (SP with θm) will be enabled (switch down). If the profile is dominated by respiratory motion, the respiratory compensation (SP with F(s)) is enabled (switch up). Alternatively, frequency analysis of the force signal combined with peak detection can be used to determine if the CF profile is dominated by cardiac or respiratory motion and automatically select which algorithm to perform for the ablation. As a further alternative, a single controller, such as an Extended Kalman Filter (EKF), Model Predictive Controller (MPC) or another predictive control algorithm, may be implemented to simultaneously compensate for multiple disturbances, including both cardiac and respiratory disturbances.

Figure 16:
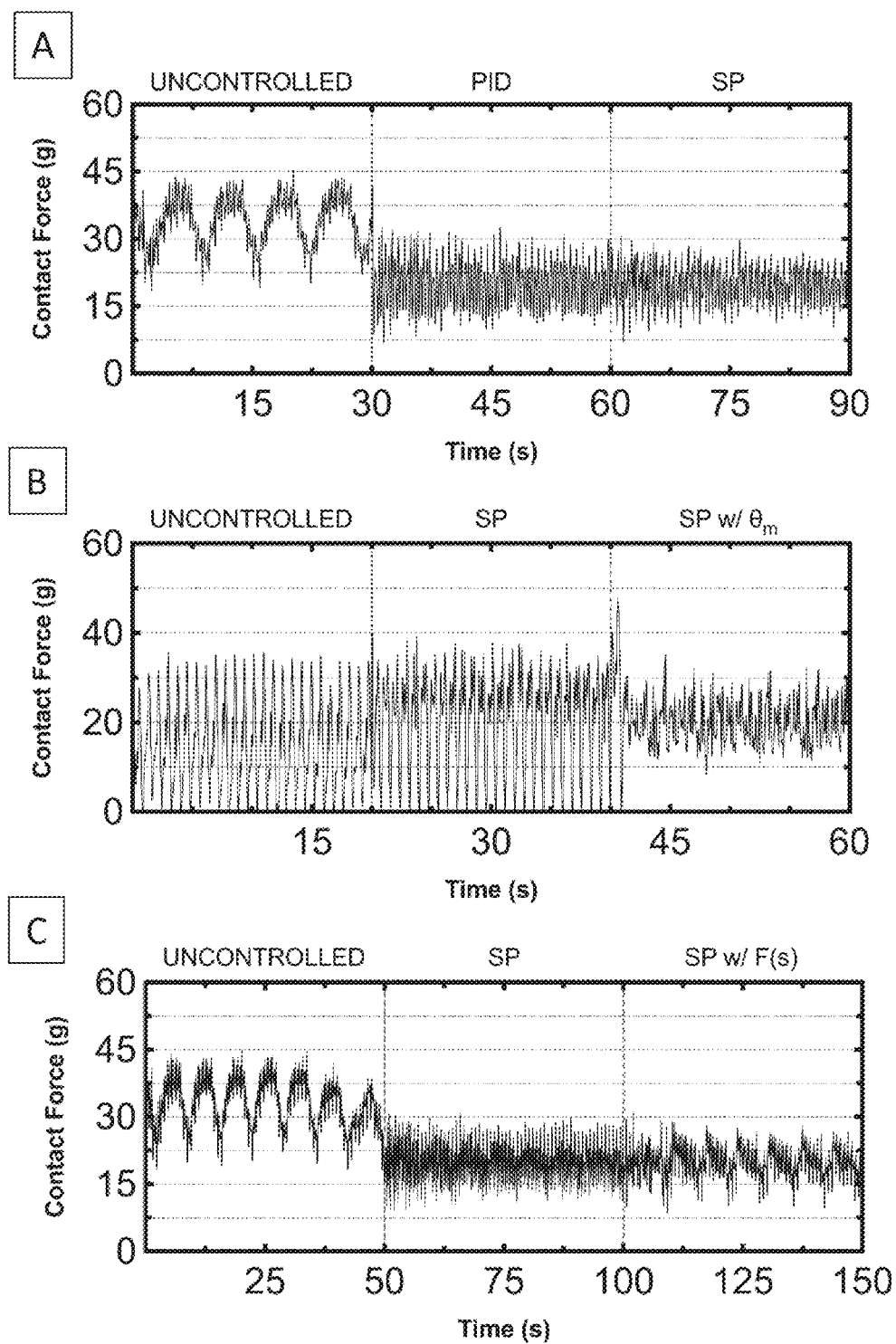
FIG. 16 (A) shows a first CF profile in a simulation using a control algorithm shown in FIG. 15, reflecting the difference between PID and Smith predictor (SP). (B) shows a second CF profile in a simulation using a control algorithm shown in FIG. 15, i.e., a simulation that shows a comparison between SP (as shown in FIG. 15B) and SP with a cardiac disturbance modifier (SP with θm.

FIG. 16 shows a series of simulations using different configurations of the control schemes shown in FIG. 15. FIG. 16A shows the difference between PID and Smith predictor (SP). FIG. 16A shows a CF profile over time. Initially the CFC is disabled and then engaged and programmed to deliver 20 g of force at the 30-second mark using PID. At the 60-second mark the controller was switched to a SP. The PID gains were optimally chosen for the large deadtime in the system. Although the SP performed only slightly better than the PID, the capability of adding modifiers to the feedback path makes the SP a superior control system.

FIG. 16B is a simulation that shows a comparison between SP (as shown in FIG. 15B) and SP with a cardiac disturbance modifier (SP with θm; as shown in FIG. 15C). Similar to the simulation shown in FIG. 16A, initially the CFC is disabled and then engaged to deliver 20 g of force at the 20-second mark using SP. At the 40-second mark, the modifier was enabled. Since the CF profile is dominated by cardiac motion, the SP with a cardiac disturbance modifier (SP with θm) is expected to perform well, which it does.

FIG. 16C is a simulation that shows a comparison between SP (as shown in FIG. 15B) and SP with a respiratory disturbance modifier (SP with F(s); as shown in FIG. 15D). Similar to the simulation shown in FIG. 16A, initially the CFC is disabled and then engaged to deliver 20 g of force at the 50-second mark using SP. The F(s) modifier is added at the 100-second mark. Since this CF profile is dominated with respiratory motion, both SP and SP with F(s) are expected to work well. However, the F(s) filter does reduce the amount of CF variation in the output force.

FIG. 17 shows recorded CF profiles from experiments involving in vivo catheter contact at various target locations in a pig heart. For these experiments, a male farm pig was prepared for catheterization. The pig was prepared with left and right femoral entry access points for catheter insertion. Target locations in the right atrium and left atrium were evaluated. For each location the catheter tip was manipulated to the target location and manually maintained to provide 20 g of force for 30 seconds, while the contact force (CF) profile was recorded. Following this, the CFC was engaged and programmed to deliver 20 g of force; the controlled CF profile was recorded. To maintain consistency, the catheter tip was not repositioned between manual and CFC-controlled profiles. The catheter-tissue incident angle was kept <30 degrees.

FIG. 17A shows results from an experiment performed in the left atrium of a pig. As the catheter comes in contact with the tissue, there are large force fluctuations due to the heart beating. When the controller—programmed to maintain 20 grams of force—is turned on (dashed line), these fluctuations drastically decrease and the contact-force level is constant. During this time the linear actuator is moving the catheter tip in synchrony with the heart and maintaining a desired level of force.

FIG. 17B shows a recorded CF profile from another experiment in the right atrium. Once again, the controller is initially disabled and then turned on (dashed line) to deliver a programmed force of 20 grams. The desired force is reduced to 10 grams at approximately 13.5 s then returns to 20 grams at 25 s demonstrating contact-force control.

The results shown in FIGS. 17A and 17B demonstrate that the cardiac compensation algorithm performs extremely well when motion is dominated by cardiac motion disturbances; which is often the case since for many ablation procedures the patient is subjected to apnea (temporarily forcing the patient to hold their breath) during catheter ablation. However, there are cases where apnea cannot be utilized and respiratory motion is dominant. In these areas the cardiac compensation algorithm does not compensate for respiratory motion disturbances adequately. FIG. 17C shows a reduction of cardiac disturbances, but little to no reduction in respiratory motion disturbances. This is another experiment performed in the left atrium of the pig.

FIG. 17D shows results from another experiment in a pig—the right atrial septum is dominated by respiratory motion while cardiac motion is minimal. The cardiac compensation controller would be ineffective in removing these low-frequency disturbances. The respiratory compensation controller was turned on (dashed line) for 20 grams of force, resulting in a significant improvement in response.

Several RF ablations were delivered in the left atrium and right atrium. Recorded CF profiles (not shown) confirm that a desired contact force was maintained during ablation delivery. Removal and inspection of the pig's heart provided visual confirmation (not shown) of ablation lesions.

Ideal control applications do not have significant deadtime in their feedback loop. Low deadtime enables high gain resulting in superior disturbance rejection. In contrast, high deadtime inhibits the response of the control and performs poorly. The integrator term in the PID controller is particularly sensitive to deadtime in the control loop. The function of this term is to continue to ramp up the controller's output so long as there is an error between a desired CF and a measured CF. Deadtime within the loop can reduce performance, may cause instability, and may lead to poor disturbance rejection. The higher the amount of deadtime in the system, the less capable the PID will be to reject output disturbances.

While PID is sensitive to deadtime, PID can provide acceptable control at lower levels of deadtime. A number of techniques are available to determine suitability of PID in a system with deadtime. For example, one approach is to determine the time constant of the real-world process G(s) and compare the time constant to the deadtime. If the deadtime of the system exceeds the time constant of the system, time-delay compensating algorithms such as a deadtime compensation or other model-based control techniques will typically perform better than PID (W. L. Wade, Basic and Advanced Regulatory Control: System Design and Application, 2004, ch. 6, pp. 136). In practice, if the deadtime exceeds more than two times the time constant a time-delay compensating algorithm such as a Smith predictor is often implemented.

For the implementation of the CFC device in the pig heart experiments shown in FIG. 17, the process model G(s) can be modeled by either a 1st- or 2nd-order transfer function, with a time constant of 30 ms or 34 ms, respectively. For this same implementation, the observed deadtime of the system (about 100 ms) exceeds the time constants by a factor of three, and based on this observation, a time-delay compensating algorithm such as the Smith predictor can offer benefit.

Another approach to determine whether PID is suitable to a particular implementation with deadtime is to inspect CF profiles obtained from simulations or experiments for indications of instability or compromised performance. For example, FIG. 18 shows several CF profiles for an implementation with a PID controller comparing the effect of deadtime on a CF profile. FIG. 18A shows several plots that may be compared for a stability analysis while FIG. 18B shows several plots that may be compared to analyze disturbance rejection.

FIG. 18A shows the step response of the process model $\hat{G}(s)$ using a PID controller with increasing deadtime in the absence of any disturbance (eg., cardiac motion and respiratory motion disturbances are not present). These simulations show that when deadtime surpasses time constant (30 ms or 34 ms as described above), the controller becomes unstable. Note the significant ringing (overshoot) when deadtime is 34 ms and the instability when deadtime is 40 ms. The deadtime in the pig experiment implementation is more than 3 times larger than time constant of the process model, and therefore would benefit from a time-delay compensating algorithm compared to a standard PID algorithm. Reducing the gains of the PID controller may mitigate the stability problem evident at 40 ms of deadtime; however the controller would then be sluggish with poor disturbance rejection.

FIG. 18B shows CF profiles that demonstrate rejection of output disturbances using a PID controller with varying deadtime. In each of the plots the disturbance is the same (note that the 45 ms and 50 ms plots are on a different scale than the other four plots), which in this simulation is modeled as a sine sweep from 0 to 2.5 Hz at 10 g peak-peak, covering a representative range of frequencies found in the heart. The plots show that when deadtime is absent (0 ms), the output CF is well regulated and maintains a desired value. Corresponding simulations with delays of 20 ms, 34 ms and 45 ms, respectively, in the feedback loop also show that output CF can be maintained on a desired value. In contrast, poor performance and instability is evident in the 45 ms and 50 ms plots. The simulations show that the system becomes unstable with only 45 ms of delay (>time constant) with disturbances in the frequency range of the heart (0.1 to 2.5 Hz). The amount of observed deadtime (averaging approximately 100 ms) present in the system in the pig experiment implementation is more than twice of the 45 ms deadtime shown in this simulation, indicating that a time-delay compensating algorithm would outperform a PID controller.

Calibration can be useful for accurately determining deadtime in a system and improving modeling of modifiers to compensate for deadtime. Accordingly, the method of controlling the CFC device can include a calibration step. Similarly, the system may include a calibrator module or component. Sophisticated catheter mapping systems are hosted on general-purpose operating systems, which process tasks with various degrees of complexity and priority. This may result in a deadtime that is not consistent from procedure-to-procedure or day-to-day. Thus, a calibrator may be used prior to each procedure, or periodically as desired. Although control systems are fairly robust, a calibration step can be advantageous in that it allows the deadtime θp to be estimated accurately to improve modeling of an estimated deadtime θpm.

In an example of a calibration step, a comparison is made between CF data received from an external ideal force sensor (strain guage) and CF data received from a force sensor located at a remote end of a catheter that is used during a medical procedure. The external ideal force sensor (strain gauge) comes in dynamic contact with the force-sensing catheter. The contact-force readings from both the strain gauge and the catheter force sensor are simultaneously recorded. A cross-correlation calculation between both contact-force data sets is used to model the estimated deadtime θpm in the system. A dedicated (separate) device can be used to do this. This calibration step can also be used to modify/correct $\hat{G}(s)$ if necessary (time constant and $\hat{G}(s)$ may vary slightly from catheter-to-catheter).

The CFC device may be used to adjust for any disturbance that may impact upon contact-force between a catheter tip and a target tissue. Disturbances of cardiac motion, respiratory motion, patient motion and catheter instability are illustrative, and other disturbances may be accommodated.

The CFC device may be used in combination with any force sensing catheter and/or any robotic system incorporating a force sensing catheter. The force sensing catheter and/or the robotic system incorporating a force sensing catheter may support any number of degrees of freedom of motion of the catheter with any number of actuators without limiting implementation of the CFC device. The CFC device can be an add-on tool compatible with commercially available, existing force-sensing catheters and sheaths.

The CFC device, and systems and methods incorporating the same may be used for medical treatment. The CFC device, and systems and methods incorporating the same may find use in any suitable catheter procedure for any suitable target tissue. RF catheter ablation is an illustrative example, of catheter ablation and other types of catheter ablation may be accommodated, including for example cryoablation. Ablation treatments incorporating the CFC device need not be limited to cardiac tissue, and may accommodate other target tissues including, for example, liver.

The CFC device may be used in combination with an imaging system providing image data of a catheter tip and/or a target tissue. Any suitable imaging system may be used including magnetic resonance imaging, x-ray computed tomography or ultrasound.

The computer-implemented control of the CFC device typically requires a memory, an interface and a processor. The types and arrangements of memory, interface and processor may be varied according to implementations. For example, the interface may include a software interface that communicates with an end-user computing device. The interface may also include a physical electronic device configured to receive requests or queries from an end-user.

Although a microprocessor or microcontroller was used in experiments described above, many other computer device types may be used including for example, a programmable logic controller or a field programmable logic/gate array. Moreover, any conventional computer architecture may be used for computer-implemented control of the CFC device including for example a memory, a mass storage device, a processor (CPU), a Read-Only Memory (ROM), and a Random-Access Memory (RAM) generally connected to a system bus of data-processing apparatus. Memory can be implemented as a ROM, RAM, a combination thereof, or simply a general memory unit. Software modules in the form of routines and/or subroutines for carrying out features of the CFC device for maintaining a desired contact-force can be stored within memory and then retrieved and processed via processor to perform a particular task or function. Similarly, one or more compensation algorithms may be encoded as a program component, stored as executable instructions within memory and then retrieved and processed via a processor. A user input device, such as a keyboard, mouse, or another pointing device, can be connected to PCI (Peripheral Component Interconnect) bus. The software will typically provide an environment that represents programs, files, options, and so forth by means of graphically displayed icons, menus, and dialog boxes on a computer monitor screen.

A data-process apparatus can include CPU, ROM, and RAM, which are also coupled to a PCI (Peripheral Component Interconnect) local bus of data-processing apparatus through PCI Host Bridge. The PCI Host Bridge can provide a low latency path through which processor may directly access PCI devices mapped anywhere within bus memory and/or input/output (I/O) address spaces. PCI Host Bridge can also provide a high bandwidth path for allowing PCI devices to directly access RAM.

A communications adapter, a small computer system interface (SCSI), and an expansion bus-bridge may also be attached to PCI local bus. The communications adapter can be utilized for connecting data-processing apparatus to a network. SCSI can be utilized to control a high-speed SCSI disk drive. An expansion bus-bridge, such as a PCI-to-ISA bus bridge, may be utilized for coupling ISA bus to PCI local bus. PCI local bus can be connected to a monitor, which functions as a display (e.g., a video monitor) for displaying data and information for an operator and also for interactively displaying a graphical user interface.

Computer-implemented control of the CFC device may accommodate any type of end-user computing device including computing devices communicating over a networked connection. The computing device may display graphical interface elements for performing the various functions of the system such as selecting a pre-set desired contact force, selecting a control algorithm, selecting a compensation algorithm, modifying an existing contact-force setting or an existing control algorithm or an existing compensation algorithm, or updating a database of an activity log that may be locally stored in the computing device. For example, the computing device may be a desktop, laptop, notebook, tablet, personal digital assistant (PDA), PDA phone or smartphone, gaming console, portable media player, and the like. The computing device may be implemented using any appropriate combination of hardware and/or software configured for wired and/or wireless communication. Communication can occur over a network, for example, where remote control or remote monitoring of the CFC device is desired.

If a networked connection is desired the CFC device and its controlling system may accommodate any type of network. The network may be a single network or a combination of multiple networks. For example, the network may include the internet and/or one or more intranets, landline networks, wireless networks, and/or other appropriate types of communication networks. In another example, the network may comprise a wireless telecommunications network (e.g., cellular phone network) adapted to communicate with other communication networks, such as the Internet. For example, the network may comprise a computer network that makes use of a TCP/IP protocol (including protocols based on TCP/IP protocol, such as HTTP, HTTPS or FTP).

The CFC device and systems incorporating the same as described herein and each variant, modification or combination thereof may be controlled by a suitable computer-implemented method. A method of controlling the CFC device includes detecting contact force data with a force sensor located at a remote end of a catheter; receiving the contact force data with a controller; and generating and communicating a control signal to the linear actuator to minimize a difference between the real-time contact force data and a preset desired contact force. For example, as described with reference to control algorithms schematically represented in FIG. 15, the method includes calculating an error between the measured output CF and the desired CF; inputting the error into the controller C(s), where an appropriate control signal is calculated; and communicating the control signal to the linear actuator of the motor with the motor response providing catheter tip movement and subsequent measurement and communication of a CF value to reinitiate and repeat the loop (the dynamics of this system, including deadtime $\theta p$, are captured in G(s)). Where a deadtime of sufficient magnitude is present the method may optionally include generating a delay-based modifier modeled on an identified time delay; and applying the delay-based modifier to the control signal. The identified time delay may be determined by identifying a time delay between the steps of detecting the contact force data and receiving the contact force data. Again with reference to FIG. 15 for example, these optional method steps for dead-time compensation include inputting the control signal to a numerical model $\hat{G}(s)$ that outputs a delay-based modifier that is an estimate of the CF value without deadtime which is then delayed by $\theta pm$, an estimate of the process delay $\theta p$ which results in a further delay-based modifier that is subtracted from the measured output CF; and then the CF value without delay is added. Further optional method steps may include applying a cardiac modifier to the control signal to compensate for cardiac motion disturbances with the cardiac modifier optionally generated by measuring a heart rate and deriving the cardiac modifier based on the heart rate. Again with reference to FIG. 15, the step of applying the cardiac modifier is illustratively shown as further delaying the estimate of the CF value without deadtime combined with $\theta pm$ by adding $\theta m$ whose purpose is to synchronize the linear actuator with the heart rate. Further optional method steps may include applying a respiratory modifier to the control signal to compensate for respiratory motion disturbances; the respiratory modifier can be a low-pass filter set to remove high frequency disturbances present in the contact force data. Further optional method steps may include receiving real-time patient specific data with the controller and using the real-time patient specific data to generate the control signal to minimize the difference between the real-time contact force data and the preset desired contact force; the real-time patient specific data may be tissue temperature at a contact point with the catheter, electrocardiogram, respiratory rate, catheter-tissue incident angle, or any combination thereof. A further optional method step may include displaying the contact force data on a computer monitor. A further optional method step may include receiving real-time imaging data of the remote end of the catheter and displaying the imaging data on the computer monitor. A further optional method step may include calculating a force-time integral (FTI), and automatically sending a control signal to retract the catheter once a preset desired FTI is reached.

The CFC device and systems incorporating the same as described herein and each variant, modification or combination thereof may also be implemented as a method or computer programmable/readable code on a non-transitory computer readable medium (i.e. a substrate). The computer readable medium is a data storage device that can store data, which can thereafter, be read by a computer system. Examples of a computer readable medium include read-only memory, random-access memory, CD-ROMs, magnetic tape, SD card, optical data storage devices and the like. The computer readable medium may be geographically localized or may be distributed over a network coupled computer system so that the computer readable code is stored and executed in a distributed fashion.

Embodiments described herein are intended for illustrative purposes without any intended loss of generality. Still further variants, modifications and combinations thereof are contemplated and will be recognized by the person of skill in the art. Accordingly, the foregoing detailed description is not intended to limit scope, applicability, or configuration of claimed subject matter.

What is claimed is:

1. A device comprising:
    a base sized to be hand-held, the base defining a longitudinal axis between first and second opposing longitudinal ends
    a cover reversibly fastened to the base in a closed position;
    a sheath clamp coupled to the base, the sheath clamp capturing a sheath handle of a sheath to immobilize the sheath handle relative to the base, the sheath clamp is an aperture formed in corresponding abutting edges of the cover and the base, the aperture being formed when the cover and the base are in the closed position;
    a catheter clamp capturing a catheter, a remote end of the catheter configured to deliver a catheterized medical procedure;
    the catheter clamp aligned to be substantially co-axial with the sheath clamp; and
    a linear actuator effecting back-and-forth linear motion of the catheter clamp and the catheter relative to the sheath clamp.

2. The device of claim 1, wherein the catheter clamp comprises a first plate mounted to the linear actuator and a second plate reversibly fastened to the first plate.

3. The device of claim 2, wherein the catheter clamp is a pipe formed in corresponding contacting surfaces of the first and the second plates, the pipe being formed when the first and second plates are in a closed position.

4. The device of claim 3, wherein the pipe provides a gripping material having a high coefficient of friction with the catheter.

5. The device of claim 1, wherein the catheter clamp is a reversibly closeable channel capturing the catheter when the reversibly closeable channel is in a closed position.

6. The device of claim 5, wherein the channel provides a gripping material having a high coefficient of friction with the catheter.

7. The device of claim 1, further comprising a guide aperture coupled to the base, the guide aperture sized to allow free sliding passage of the catheter, the guide aperture substantially co-axial with the catheter clamp and the sheath clamp.

8. The device of claim 7, wherein the sheath clamp is located at the first longitudinal end, the guide aperture is located at the second longitudinal end and the catheter clamp is located therebetween.

9. The device of claim 8, wherein the guide aperture is formed in corresponding abutting edges of the cover and the base, the guide aperture being formed when the cover and the base are in a closed position.

10. The device of claim 1, further comprising a guide aperture, the guide aperture formed in corresponding abutting edges of the cover and the base, the guide aperture being formed when the cover and the base are in a closed position.

11. The device of claim 1, further comprising a side port aperture coupled to the base, the side port aperture sized to receive a side port extending radially from the sheath handle.

12. The device of claim 11, wherein an axis of the side port aperture is substantially perpendicular to an axis of the aperture that forms the sheath clamp.

13. The device of claim 1, wherein the linear actuator is a sled and slide track mechanism.

14. The device of claim 1, wherein the linear actuator is a coil assembly mounted on a magnetic rod.

15. The device of claim 1, further comprising a first limit switch mounted to the first longitudinal end of the base and a second limit switch mounted to the second longitudinal end of the base.

16. The device of claim 1, further comprising an encoder for tracking motion of the linear actuator.

17. The device of claim 1, further comprising a connector port mounted to the base.

18. The device of claim 17, wherein the connector port is accessible from an exterior surface of the base and the connector port is configured to receive a connector cable for electronic communication with a controller.

19. The device of claim 17, wherein the connector port is accessible from an exterior surface of the base and the connector port is configured to receive a connector cable for a driver circuit of the linear actuator.

20. The device of claim 1, wherein the sheath clamp comprises one or more jaws extending from the device at the aperture of the sheath clamp, the one or more jaws mating with a tubular body of the sheath handle.

* * * * *